(12) United States Patent
Anto et al.

(10) Patent No.: US 12,385,893 B2
(45) Date of Patent: Aug. 12, 2025

(54) APPARATUSES, COMPUTER-IMPLEMENTED METHODS, AND COMPUTER PROGRAM PRODUCTS FOR ACCURATE EXPLOSION PREDICTING AND WARNING

(71) Applicant: Honeywell International Inc., Charlotte, NC (US)

(72) Inventors: Agnel Anto, Bangalore (IN); Surya Lakshmi Subba Rao Pilla, Tadepalligudem (IN); Priyanka Sanjay Vispute, Bangalore (IN)

(73) Assignee: Honeywell International Inc., Charlotte, NC (US)

( * ) Notice: Subject to any disclaimer, the term of this patent is extended or adjusted under 35 U.S.C. 154(b) by 388 days.

(21) Appl. No.: 17/664,802

(22) Filed: May 24, 2022

(65) Prior Publication Data
US 2023/0408476 A1     Dec. 21, 2023

(51) Int. Cl.
*G01N 33/00*     (2006.01)
*G06F 18/2415*     (2023.01)
*G06F 18/25*     (2023.01)

(52) U.S. Cl.
CPC ..... *G01N 33/0075* (2013.01); *G01N 33/0063* (2013.01); *G06F 18/2415* (2023.01); *G06F 18/251* (2023.01); *G01N 33/0068* (2024.05)

(58) Field of Classification Search
CPC .......... G01N 33/0075; G01N 33/0063; G01N 33/0068; G01N 33/0062; G01N 2030/025; G01N 2030/0095; G01N 2030/8804; G08B 21/182; G08B 21/16; G08B 17/00; G08B 17/125; G08B 17/12; G08B 31/00;
(Continued)

(56) References Cited

U.S. PATENT DOCUMENTS 11,164,134 B2 * 11/2021 Barak ................ G06Q 10/0635
2018/0209853 A1 * 7/2018 Kraus .................... G01N 21/72
2022/0121884 A1 * 4/2022 Zadeh .................... G06N 3/006

FOREIGN PATENT DOCUMENTS

CN     102426753 A  *  4/2012
CN     105336085 A  *  2/2016  ........... G08B 17/125
(Continued)

OTHER PUBLICATIONS

Extended European Search Report Mailed on Oct. 18, 2023 for EP Application No. 23170915, 9 page(s).
(Continued)

*Primary Examiner* — Jeffrey P Aiello
(74) *Attorney, Agent, or Firm* — Alston & Bird LLP

(57) ABSTRACT

Embodiments utilize captured data, such as gas data and/or flame/heat data, from sensors in an environment to generate a data-constructed image for use in predicting explosion likelihood within an environment. Some embodiments utilize gas and flame data to generate the data-constructed image that is processable via one or more model(s) to determine whether the environment includes one or more sub-regions at risk of explosion. Some embodiments receive a plurality of gas sensor data and a plurality of flame sensor data, generate a data-constructed image including a plurality of channels based at least in part on such data, and generate explosion prediction data by applying at least a portion of the data-constructed image to a prediction model.

19 Claims, 12 Drawing Sheets

(58) Field of Classification Search
CPC ... G08B 19/00; G06F 18/2415; G06F 18/251;
F23N 5/003; F23N 2231/20; G06N 3/02;
G06N 3/088; G06N 3/08; G06N 3/045;
G06N 20/00; G08C 2201/51; G06T
2207/10028; G06T 1/00
USPC ............... 340/506, 517, 521, 584, 632, 540;
374/121; 382/159; 700/28, 44, 45, 83;
702/181, 182, 24, 28, 32, 1, 128, 130,
702/132, 188, 179, 26, 30, 127, 23;
706/12
See application file for complete search history.

(56) References Cited

FOREIGN PATENT DOCUMENTS

| CN | 111899460 A | * | 11/2020 | ......... G06K 9/00711 |
|----|-------------|---|---------|------------------------|
| KR | 20220104613 A | * | 4/2021 | ............. G08B 17/12 |
| WO | WO-2008105578 A1 | * | 9/2008 | ............. G06Q 50/04 |

OTHER PUBLICATIONS

EP Office Action Mailed on Oct. 21, 2024 for EP Application No. 23170915, 4 page(s).
Communication about intention to grant a European patent Mailed on Jun. 24, 2025 for EP Application No. 23170915, 6 page(s).

* cited by examiner

APPARATUSES, COMPUTER-IMPLEMENTED METHODS, AND COMPUTER PROGRAM PRODUCTS FOR ACCURATE EXPLOSION PREDICTING AND WARNING

TECHNICAL FIELD

Embodiments of the present disclosure generally are directed to accurately predicting whether an explosion may occur in an environment, and specifically to utilizing gas sensor data and flame/heat sensor data to accurately predict an explosion may occur in the environment.

BACKGROUND

In various contexts, an environment may be exposed to a possibility of explosion. For example, in some contexts, dangerous circumstances may lead to the presence of ingredients that could cause an explosion. Monitoring such ingredients is important to prevent harm to person(s) in an environment and/or the environment itself, however accurately predicting a likelihood of explosion and/or time until explosion is useful in remediating or avoiding such harmful circumstances.

Inventors have discovered problems with current implementations for accurately predicting explosions. Through applied effort, ingenuity, and innovation, the inventors have solved many of these problems by developing the solutions embodied in the present disclosure, the details of which are described further herein.

BRIEF SUMMARY

In one aspect, a computer-implemented method includes receiving a plurality of gas sensor data and a plurality of flame sensor data, generating a data-constructed image includes a plurality of channels, the plurality of channels includes at least a first channel assigned based at least in part on the plurality of gas sensor data and at least one additional channel assigned based at least in part on the plurality of flame sensor data, and generating explosion prediction data by applying at least a portion of the data-constructed image to a prediction model, where the prediction model generates the explosion prediction data based at least in part on explosion feature data determined from at least the plurality of channels corresponding to at least a portion of the data-constructed image.

The computer-implemented method may also include the computer-implemented method further includes applying the data-constructed image to a computer vision model that identifies at least the portion of the data-constructed image determined associated with at least one explosion contribution level indicating presence of at least one explosion contributing factor in an environment, and extracting the portion of the data-constructed image from the data-constructed image, where the prediction model only processes the extracted portion of the data-constructed image.

The computer-implemented method may also include where the plurality of gas sensor data includes at least a first gas sensor data portion and a second gas sensor data portion captured via a first gas sensor, and where the plurality of gas sensor data includes a first gas sensor data portion associated with a first sampling rate, and where the plurality of flame sensor data includes at least a first flame sensor portion captured via a first flame sensor associated with a second sampling rate, where the first sampling rate is faster than the second sampling rate, and where generating the data-constructed image includes generating an averaged value by averaging the first gas sensor data portion and the second gas sensor data portion, and assigning at least a first pixel of the first channel based at least in part on the averaged value.

The computer-implemented method may also include where the plurality of gas sensor data includes at least a first gas sensor data portion captured via a first gas sensor, and where the plurality of gas sensor data includes a first gas sensor data portion associated with a first sampling rate, and where the plurality of flame sensor data includes at least a first flame sensor portion and a second flame sensor portion captured via a first flame sensor associated with a second sampling rate, where the second sampling rate is faster than the first sampling rate, and where generating the data-constructed image includes generating an averaged value by averaging the first flame sensor data portion and the second flame sensor data portion, and assigning at least a first pixel of an additional channel of the plurality of additional channels based at least in part on the averaged value.

The computer-implemented method may also include where the plurality of gas sensor data includes a first time series of gas sensor data portions captured via at least one gas sensor, and where generating the data-constructed image includes assigning a first pixel value of the first channel based at least in part on a first gas sensor data portion of the first time series of gas sensor data portions corresponding to a first timestamp, and assigning each subsequent pixel value of the first channel based at least in part on a next gas sensor data portion associated with each subsequent timestamp.

The computer-implemented method may also include where the plurality of flame sensor data includes at least first band range data, second band range data, and third band range data, where the at least one additional channel includes a second channel, a third channel, and a fourth channel, and where generating the data-constructed image includes assigning the second channel based at least in part on the first band range data, assigning the third channel based at least in part on the second band range data, and assigning the fourth channel based at least in part on the third band range data.

The computer-implemented method may also include the computer-implemented method further includes applying the data-constructed image to a computer vision model that at least determines an explosion contribution level, and determining the explosion contribution level satisfies a threshold, where the generating the explosion likelihood data is initiated in response to determining that the explosion contribution level satisfies the threshold.

The computer-implemented method may also include where the plurality of gas sensor data is collected via a plurality of gas sensors.

The computer-implemented method may also include where the plurality of flame sensor data is collected via a plurality of flame sensors.

The computer-implemented method may also include where the plurality of gas sensor data includes at least a first gas data portion associated with a first gas sensor corresponding to a first environment region and a second gas data portion associated with a second gas sensor corresponding to a second environment region, and where the plurality of flame sensor data includes a first flame data portion associated with a first flame sensor corresponding to the first environment region and a second flame data portion associated with a second flame data portion corresponding to the second environment region, where generating the data-constructed image includes generating a first sub-image corresponding to the first environment region based at least in part on the first gas data portion and the first flame data portion, generating a second sub-image corresponding to the second environment region based at least in part on the second gas data portion and the second flame data portion, and generating the data-constructed image by assigning a first portion of the data-constructed image to the first sub-image and assigning a second portion of the data-constructed image to the second sub-image.

The computer-implemented method may also include where the data-constructed image includes a plurality of sub-image, each sub-image corresponding to an assigned pixel sub-region of the data-constructed image.

The computer-implemented method may also include where the explosion prediction data includes a data value indicating a probability of an explosion.

The computer-implemented method may also include the computer-implemented method further includes determining the explosion prediction data satisfies a threshold by at least comparing the explosion prediction data to the threshold, and in response to determining the explosion prediction data satisfies the threshold, generating a warning signal.

The computer-implemented method may also include where the prediction model includes a specially trained machine learning model. Other technical features may be readily apparent to one skilled in the art from the following figures, descriptions, and claims.

In one aspect, an apparatus includes at least one processor. The apparatus also includes at least one memory storing instructions that, when executed by the processor, configure the apparatus to receive a plurality of gas sensor data and a plurality of flame sensor data, generate a data-constructed image includes a plurality of channels, the plurality of channels includes at least a first channel assigned based at least in part on the plurality of gas sensor data and at least one additional channel assigned based at least in part on the plurality of flame sensor data, and generate explosion prediction data by applying at least a portion of the data-constructed image to a prediction model, where the prediction model generates the explosion prediction data based at least in part on explosion feature data determined from at least the plurality of channels corresponding to at least a portion of the data-constructed image.

The apparatus may also be configured where the plurality of flame sensor data includes at least first band range data, second band range data, and third band range data, where the at least one additional channel includes a second channel, a third channel, and a fourth channel, and where generating the data-constructed image includes assign the second channel based at least in part on the first band range data, assign the third channel based at least in part on the second band range data, and assign the fourth channel based at least in part on the third band range data.

The apparatus may also be configured where the instructions further configure the apparatus to apply the data-constructed image to a computer vision model that at least determines an explosion contribution level, and determine the explosion contribution level satisfies a threshold, where the generating the explosion likelihood data is initiated in response to determining that the explosion contribution level satisfies the threshold.

The apparatus may also include where the plurality of gas sensor data includes at least a first gas data portion associated with a first gas sensor corresponding to a first environment region and a second gas data portion associated with a second gas sensor corresponding to a second environment region, and where the plurality of flame sensor data includes a first flame data portion associated with a first flame sensor corresponding to the first environment region and a second flame data portion associated with a second flame data portion corresponding to the second environment region, where generating the data-constructed image includes generate a first sub-image corresponding to the first environment region based at least in part on the first gas data portion and the first flame data portion, generate a second sub-image corresponding to the second environment region based at least in part on the second gas data portion and the second flame data portion, and generate the data-constructed image by assigning a first portion of the data-constructed image to the first sub-image and assigning a second portion of the data-constructed image to the second sub-image. Other technical features may be readily apparent to one skilled in the art from the following figures, descriptions, and claims.

In one aspect, a non-transitory computer-readable storage medium, the computer-readable storage medium including instructions that when executed by at least one processor, cause the at least one processor to receive a plurality of gas sensor data and a plurality of flame sensor data, generate a data-constructed image includes a plurality of channels, the plurality of channels includes at least a first channel assigned based at least in part on the plurality of gas sensor data and at least one additional channel assigned based at least in part on the plurality of flame sensor data, and generate explosion prediction data by applying at least a portion of the data-constructed image to a prediction model, where the prediction model generates the explosion prediction data based at least in part on explosion feature data determined from at least the plurality of channels corresponding to at least a portion of the data-constructed image.

The computer-readable storage medium may also include where the plurality of gas sensor data includes at least a first gas data portion associated with a first gas sensor corresponding to a first environment region and a second gas data portion associated with a second gas sensor corresponding to a second environment region, and where the plurality of flame sensor data includes a first flame data portion associated with a first flame sensor corresponding to the first environment region and a second flame data portion associated with a second flame data portion corresponding to the second environment region, where generating the data-constructed image includes generate a first sub-image corresponding to the first environment region based at least in part on the first gas data portion and the first flame data portion, generate a second sub-image corresponding to the second environment region based at least in part on the second gas data portion and the second flame data portion, and generate the data-constructed image by assigning a first portion of the data-constructed image to the first sub-image and assigning a second portion of the data-constructed image to the second sub-image. Other technical features may be readily apparent to one skilled in the art from the following figures, descriptions, and claims.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
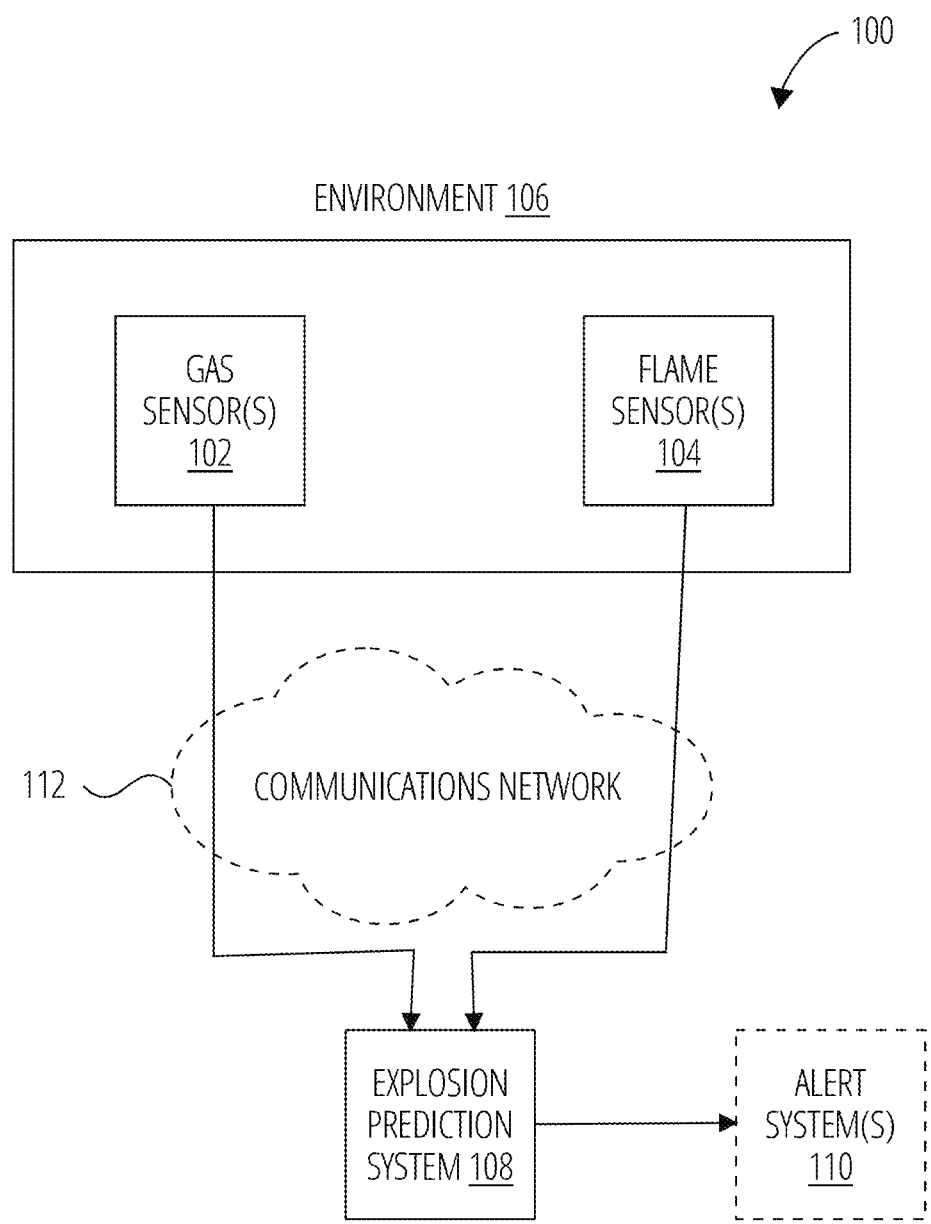
FIG. 1 illustrates an example system for explosion predicting in accordance with at least some example embodiments of the present disclosure.

Embodiments of the present disclosure now will be described more fully hereinafter with reference to the accompanying drawings, in which some, but not all, embodiments of the disclosure are shown. Indeed, embodiments of the disclosure may be embodied in many different forms and should not be construed as limited to the embodiments set forth herein, rather, these embodiments are provided so that this disclosure will satisfy applicable legal requirements. Like numbers refer to like elements throughout.

Overview

In various contexts, an environment may become at risk of explosion. Such an explosion (or explosions) in an environment can cause a myriad of problems, including risk to property in the environment, risk to the safety of users in the environment, or a combination of both. To avoid catastrophe, predicting whether an explosion may occur in the environment can be essential. Accurate predictions become essential in key moments, such as when a probability of explosion is rapidly increasing, thus increasing the risk of harm to person(s) and/or thing(s) in the environment.

In one example context, an environment may be at risk of explosion due to presence of particular ingredient components that, when combined, can trigger an explosion. Examples of such ingredients include various gas concentration(s), heat, spark(s), and/or the like. These ingredients may combine to cause an explosion, such that the presence of each ingredient becomes highly relevant to indicating the likelihood of an explosion occurring. The existence of various ingredients alone, however, may not provide an accurate representation of a probability of future explosion in certain contexts. For example, the concentration and/or presence of a particular ingredient rapidly increasing or decreasing may be indicative of whether the a subsequent explosion is likely.

Attempting to predict an explosion using other analysis may be subjected to different types of problems. For example, mere image processing of captured images depicting the environment may be exposed to physical blockages in the environment (e.g., smoke, debris, and/or the like) that prevent capturing of an image accurately representing the environment. In a circumstance where an image cannot be captured that accurately represents the environment in question, such implementations can quickly become inaccurate or entirely useless. As such, alternative methodologies that are less exposed to errors are desirable.

Embodiments of the present disclosure provide for improved accuracy predicting of a likelihood of an explosion in an environment. Some embodiments utilize particular data monitored from within the environment to construct a particular image, specifically a data-constructed image. The data-constructed image may be specifically constructed in a manner that utilizes data indicating presence and/or concentration of particular explosion contributing factor(s), such as presence of particular ingredient(s) that contribute to a possible explosion in the environment. In this regard, the image representation of such data is processable using one or more image processing technique(s) to determine an explosion prediction (e.g., a likelihood, probability, or other indication). In some embodiments, at least a portion of the data-constructed image is processable by one or more specially trained machine-learning, algorithmic, and/or statistical models that determine particular portions of the environment that are at-risk for explosion, and/or generate explosion prediction data associated with a likelihood of an explosion in at least a portion of the environment. By utilizing the data-constructed image and image processing methodologies described herein, embodiments of the present disclosure generate more accurate predictions as to whether a particular environment is likely to explode.

In one example embodiment, gas sensor(s) and flame sensor(s) from within an environment are utilized to generate a data-constructed image. The data-constructed image may be generated such that the data captured from each of the sensor(s) is utilized to assign pixel values of a particular channel of the data-constructed image. For example, gas sensor data from a particular gas sensor, or multiple gas sensors in a particular portion of an environment, may be utilized to capture data sample(s) and/or otherwise generate data value(s) at a particular sampling rate, and assign particular pixel value(s) sequentially within particular portions of the data-constructed image based on the captured data value(s). By constructing data-constructed images with various channels, individual data types may be assigned to different channels, resulting in a single multi-channel image with each of the different relevant data types. Similarly, features may be constructed associated with any and/or all combinations of channels of the data-constructed image for purposes of subsequent image processing.

Embodiments of the present disclosure provide various technical advantages. Some embodiments utilize specialized image processing of data-constructed image constructed from non-image data captured from within the environment to generate a more accurate prediction than alternative implementations. Additionally or alternatively, some embodiments utilize data-constructed image(s) constructed from non-image data that is significantly more difficult (or impossible) to prevent capture of via the corresponding sensor(s), for example gas and/or flame sensors, thereby increasing the likelihood of being able to accurately complete the process. Additionally or alternatively still, some embodiments utilize particular data, such as gas sensor data and/or flame sensor data, that is captured by existing sensors within the environment and/or leveraged for other purposes, such that additional sensors need not be positioned within the environment for the purpose of performing such a prediction. Additionally or alternatively still, some embodiments utilize the multi-channel nature of images to process multiple relevant data values and/or derive features associated with the individual values or combination thereof for modeling.

Example Systems and Apparatuses of the Disclosure

FIG. 1 illustrates an example system in which embodiments of the present disclosure can operate. Specifically, FIG. 1 depicts an example system 100. The system 100 may be utilized to facilitate predicting explosion prediction data, for example representing a likelihood or other determination that an explosion may occur in an environment, using a data-constructed image generated based at least in part on data captured from the environment. As illustrated, the system 100 includes gas sensor(s) 102, flame sensor(s) 104, explosion prediction system 108, and alert system(s) 110. The gas sensor(s) 102, flame sensor(s) 104, and/or optional alert system(s) 110 in some embodiments are located within a particular environment 106. In some embodiments, the explosion prediction system 108 is located externally from the environment 106, for example in a remote data center, headquarters, or the like. Alternatively, or additionally, in some embodiments, the explosion prediction system 108 is located within the environment 106 (e.g., as an on-premises system). In some embodiments, optionally the components in the environment 106 (e.g., the gas sensor(s) 102, flame sensor(s) 104, and/or optionally the alert system(s) 110).

The gas sensor(s) 102 includes one or more device(s) that capture sample(s) from an environment, and/or determine value(s) indicating presence, concentrations, volumes, and/or the like of one or more gas type(s) from the sample(s). The gas sensor(s) 102 in some embodiments capture sample(s) at a particular sampling rate, which may be the same or differ between each gas sensor of the gas sensor(s) 102. In some embodiments, each gas sensor of the gas sensor(s) 102 is configured to detect particular gas type(s), for example a predetermined set of gas type(s). In some embodiments, the gas sensor(s) 102 generate gas sensor data indicating a concentration of oxygen that may contribute to an explosion, a concentration of one or more fuel gas type(s) that may contribute to an explosion, and/or the like, or a combination thereof (e.g., capturing multiple data values). In some embodiments, the gas sensor(s) 102 includes one or more infrared sensor(s), chemical-resistor sensor(s), and/or the like, to capture and/or otherwise generate gas sensor data from each of the gas sensor(s) 102. Non-limiting examples of gas sensor data captured by the gas sensor(s) 102 include concentration(s) of particular gas type(s), indication of whether particular gas type(s) is/are present, and/or the like. In some embodiments, the gas sensor(s) 102 include a plurality of gas sensors located at different sub-regions of the environment 106. For example, in some embodiments, the gas sensor(s) 102 include at least one gas sensor in each sub-region of a particular environment.

The flame sensor(s) 104 includes one or more devices(s) that capture sample(s) from an environment, and/or determine value(s) indicating whether a flame, heat, and/or spark is present within the sample. In some embodiments, each flame sensor of the flame sensor(s) 104 is configured to detect particular data that indicates existence of a flame represented in a captured sample. The flame sensor(s) 104 in some embodiments capture sample(s) at a particular sampling rate, which may be the same or differ between each flame sensor of the flame sensor(s) 104. In some embodiments, the flame sensor(s) 104 includes one or more infrared, visible light sensors (e.g., photocells), ultraviolet sensors, and/or the like, to capture and/or otherwise generate flame sensor data from each of the flame sensor(s) 104. Non-limiting examples of flame sensor data captured by the flame sensor(s) 104 include infrared data, temperature data, and/or the like. In some embodiments, the flame sensor(s) 104 include a plurality of flame sensors located at different sub-regions of the environment 106. For example, in some embodiments, the flame sensor(s) 104 include at least one flame sensor in each sub-region of a particular environment.

In one example context, the gas sensor(s) 102 and/or flame sensor(s) 104 may be pre-existing within the environment 106 before configuration and/or installation of the associated explosion prediction system 108. For example, the explosion prediction system 108 may leverage the data-collecting capabilities of any of the exiting gas sensor(s) 102 and/or flame sensor(s) 104, such that the explosion prediction system 108 is retrofit into the existing system. In this regard, some embodiments described herein for example advantageously perform the described explosion predicting process(es) without requiring any specialized sensor(s), and without requiring that the environment 106 be upgraded to include any particular new sensors. It will be appreciated that the explosion prediction system 108 may be specially configured to process particular data, for example gas sensor data and/or flame sensor data, of a particular type, format, and/or the like that is consistent with the types of sensors within the environment 106.

The explosion prediction system 108 includes one or more computing device(s) embodied in hardware, software, firmware, and/or a combination thereof, that performs explosion predicting. For example, in some embodiments, the explosion prediction system 108 includes at least one server, at least one datastore, and/or a combination thereof. The at least one server and/or the at least one datastore may be specially configured via software, hardware, firmware, and/or a combination thereof, to perform the functionality described herein. In some embodiments, the at least one server includes at least one application server specially configured to execute functionality of at least one software application. Additionally or alternatively, in some embodiments the at least one datastore is specially configured to provide data storage and/or retrieval functionality utilized by the at least one software application. In some embodiments, the explosion prediction system 108 provides functionality for performing explosion predicting by generating explosion prediction data from captured data. For example, in some embodiments the explosion prediction system 108 receives and/or stores data captured from within the environment 106, for example gas sensor data from the gas sensor(s) 102 and/or flame sensor data from the flame sensor(s) 104, and processes such data to perform explosion predicting by generating explosion prediction data as described further herein. In this regard, the explosion prediction system 108 may perform such explosion predicting utilizing one or mode model(s), such as one or more computer vision model(s) and/or prediction model(s) as described herein. Additionally or alternatively, in some embodiments, the explosion prediction system 108 initiates outputting of alert(s) based at least in part on the results of such explosion predicting, for example based at least in part on explosion prediction data.

In some embodiments, the explosion prediction system 108 performs requesting and/or reception of sensor data from one or more sensor(s) within a particular environment. For example, in some embodiments the explosion prediction system 108 requests and/or receives gas sensor data from the gas sensor(s) 102 and/or flame sensor data from the flame sensor(s) 104, and stores such data indicating which sensor each portion of data was received from and/or a particular sub-region associated with the data, and/or other metadata utilized for identifying and/or processing such data (e.g., timestamp data when data was captured, transmitted, and/or received by the explosion prediction system 108). In some embodiments, the explosion prediction system 108 utilizes captured data to generate a data-constructed image, and process the data-constructed image utilizing one or more model(s) to generate explosion prediction data and/or perform one or more intermediary processing steps (e.g., determining explosion contribution level(s) for different sub-regions of the environment 106).

In some embodiments, the explosion prediction system 108 includes one or more display(s), speaker(s), and/or other component(s) or device(s) that enable output to a user. For example, in some embodiments such display(s) include a monitor, adaptive touchscreen, and/or the like that outputs visual user interface data. Additionally or alternatively, in some embodiments, the explosion prediction system 108 includes one or more device(s), peripheral(s), and/or other component(s) for receiving user input, such as for initiating the explosion predicting process(es) described herein. Alternatively or additionally, in some embodiments the explosion prediction system 108 includes or is communicable with one or more front-end device(s) (e.g., user device(s)) that enable interaction with the functionality of the explosion prediction system 108.

In some embodiments, the system 100 includes one or more optional alert system(s) 110. The alert system(s) 110 includes one or more computing device(s) embodied in hardware, software, firmware, and/or a combination thereof, that perform outputting of one or more alert(s). Such alert(s) may include visual alert(s), audio alert(s), physical alert(s) or data alert(s) (e.g., activation of particular systems within the environment), and/or the like based on the results of explosion predicting. In some embodiments, the alert system(s) 110 include an alarm system that activates audio sirens, visual flashing warning devices, speakers, and/or the like, that indicate an explosion is determined likely or sufficiently imminent, and/or to evacuate. Additionally or alternatively, in some embodiments the alert system(s) 110 includes end user device(s), such that the outputted alert(s) include audio output, user interfaces, notifications, and/or the like via such end user device(s) to notify maintenance users, administrators, and/or other person(s) associated with the environment 106 of the likelihood of an explosion in a particular environment, and/or that an explosion is determined likely or sufficiently imminent. In some embodiments one or more alert system of the alert system(s) 110 is/are located within the environment 106, and/or in other embodiments one or more alert system of the alert system(s) 110 is/are located external from the environment 106, or any combination thereof.

The optional communications network 112 in some embodiments is embodied in any of a myriad of network configurations. In some embodiments, the communications network 112 embodies a public network (e.g., the Internet). In some embodiments, the communications network 112 embodies a private network (e.g., an internal, localized, or closed-off network between particular devices). In some other embodiments, the communications network 112 embodies a hybrid network (e.g., a network enabling internal communications between particular connected devices and external communications with other devices). The communications network 112 in some embodiments includes one or more base station(s), relay(s), router(s), switch(es), cell tower(s), communications cable(s) and/or associated routing station(s), and/or the like. In some embodiments, the communications network 112 includes one or more user controlled computing device(s) (e.g., a user owner router and/or modem) and/or one or more external utility devices (e.g., Internet service provider communication tower(s) and/or other device(s)).

The computing device(s) each may communicate over a whole or a portion of one or more communications networks, such as the communications network 112. For example, each of the components of the system communicatively coupled to transmit data to and/or receive data from, for example, one another over the same or different wireless or wired networks embodying the communications network 112. Such configuration(s) include, without limitation, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, stand-alone entities communicating over the communications network 112, the various embodiments are not limited to this particular architecture. In other embodiments, one or more computing entities share one or more components, hardware, and/or the like, or otherwise are embodied by a single computing device such that connection(s) between the computing entities are over the communications network 112 are altered and/or rendered unnecessary. Alternatively or additionally still, in some embodiments the communications network 112 is embodied by wired connections between the gas sensor(s) 102 and/or flame sensor(s) 104, such that a wireless communications network is not required.

Figure 2:
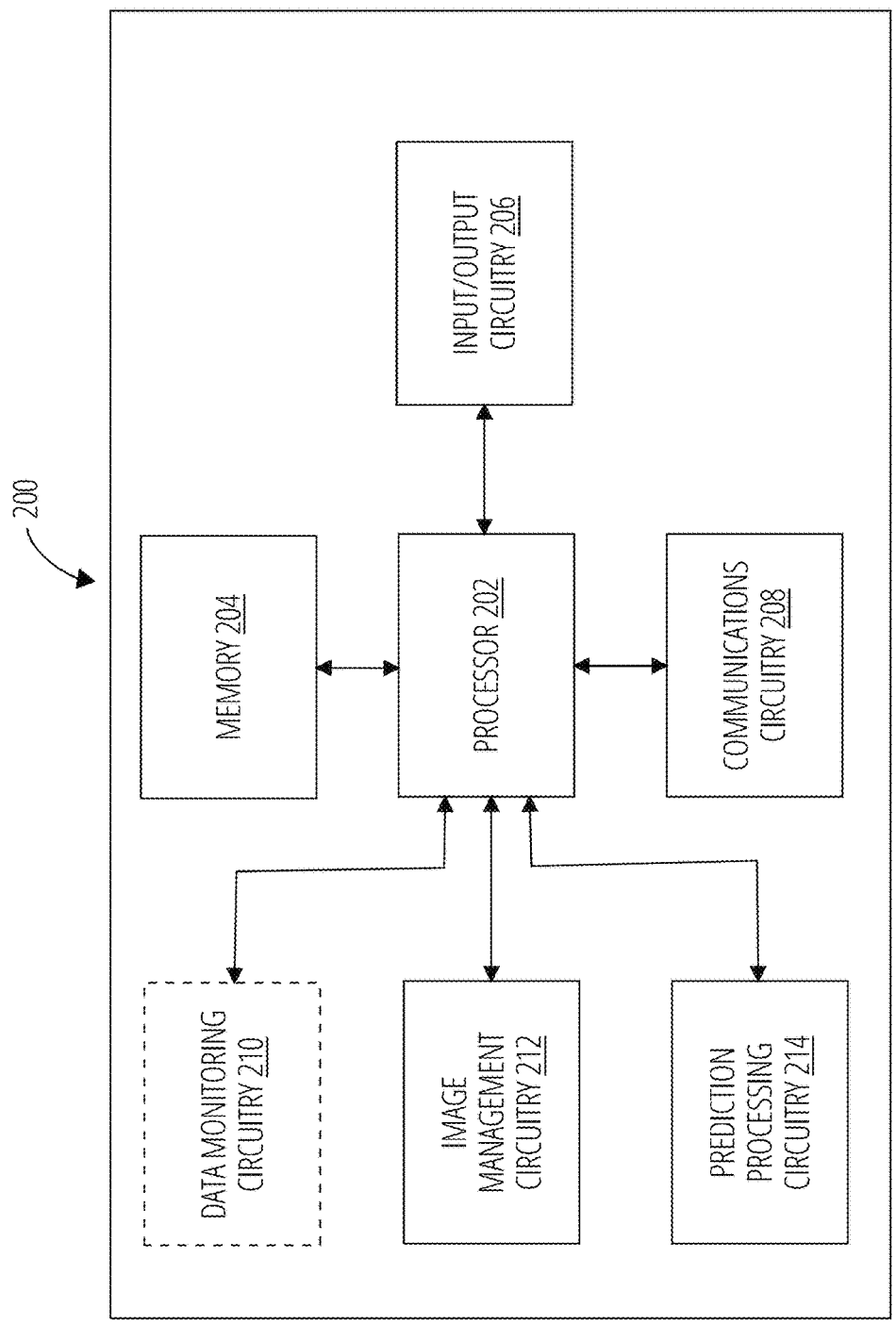
FIG. 2 illustrates an example explosion prediction apparatus in accordance with at least some example embodiments of the present disclosure.

FIG. 2 illustrates an example explosion predicting apparatus in accordance with at least some example embodiments of the present disclosure. Specifically, FIG. 2 depicts an example explosion predicting apparatus 200 ("apparatus 200") specially configured in accordance with at least some example embodiments of the present disclosure. In some embodiments, the explosion prediction system 108 and/or a portion thereof is embodied by one or more system(s), such as the apparatus 200 as depicted and described in FIG. 2. Alternatively or additionally, in some embodiments, a single computing system embodying a combination of explosion prediction system 108 and/or alert system(s) 110, such as the apparatus 200 as depicted and described in FIG. 2. The apparatus 200 includes processor 202, memory 204, input/ output circuitry 206, communications circuitry 208, optional data monitoring circuitry 210, image management circuitry 212, and prediction processing circuitry 214. In some embodiments, the apparatus 200 is configured, using one or more of the sets of circuitry 202, 204, 206, 208, 210, 212, and/or 214, to execute and perform the operations described herein.

In general, the terms computing entity (or "entity" in reference other than to a user), device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably. In this regard, the apparatus 200 embodies a particular, specially configured computing entity transformed to enable the specific operations described herein and provide the specific advantages associated therewith, as described herein.

Although components are described with respect to functional limitations, it should be understood that the particular implementations necessarily include the use of particular computing hardware. It should also be understood that in some embodiments certain of the components described herein include similar or common hardware. For example, in some embodiments two sets of circuitry both leverage use of the same processor(s), network interface(s), storage medium(s), and/or the like, to perform their associated functions, such that duplicate hardware is not required for each set of circuitry. The use of the term "circuitry" as used herein with respect to components of the apparatuses described herein should therefore be understood to include particular hardware configured to perform the functions associated with the particular circuitry as described herein.

Particularly, the term "circuitry" should be understood broadly to include hardware and, in some embodiments, software for configuring the hardware. For example, in some embodiments, "circuitry" includes processing circuitry, storage media, network interfaces, input/output devices, and/or the like. Alternatively or additionally, in some embodiments, other elements of the apparatus 200 provide or supplement the functionality of another particular set of circuitry. For example, the processor 202 in some embodiments provides processing functionality to any of the sets of circuitry, the memory 204 provides storage functionality to any of the sets of circuitry, the communications circuitry 208 provides network interface functionality to any of the sets of circuitry, and/or the like.

In some embodiments, the processor 202 (and/or co-processor or any other processing circuitry assisting or otherwise associated with the processor) is/are in communication with the memory 204 via a bus for passing information among components of the apparatus 200. In some embodiments, for example, the memory 204 is non-transitory and may include, for example, one or more volatile and/or non-volatile memories. In other words, for example, the memory 204 in some embodiments includes or embodies an electronic storage device (e.g., a computer readable storage medium). In some embodiments, the memory 204 is configured to store information, data, content, applications, instructions, or the like, for enabling the apparatus 200 to carry out various functions in accordance with example embodiments of the present disclosure.

The processor 202 may be embodied in a number of different ways. For example, in some example embodiments, the processor 202 includes one or more processing devices configured to perform independently. Additionally or alternatively, in some embodiments, the processor 202 includes one or more processor(s) configured in tandem via a bus to enable independent execution of instructions, pipelining, and/or multithreading. The use of the terms "processor" and "processing circuitry" should be understood to include a single core processor, a multi-core processor, multiple processors internal to the apparatus 200, and/or one or more remote or "cloud" processor(s) external to the apparatus 200.

In an example embodiment, the processor 202 is configured to execute instructions stored in the memory 204 or otherwise accessible to the processor. Alternatively or additionally, the processor 202 in some embodiments is configured to execute hard-coded functionality. As such, whether configured by hardware or software methods, or by a combination thereof, the processor 202 represents an entity (e.g., physically embodied in circuitry) capable of performing operations according to an embodiment of the present disclosure while configured accordingly. Alternatively or additionally, as another example in some example embodiments, when the processor 202 is embodied as an executor of software instructions, the instructions specifically configure the processor 202 to perform the algorithms embodied in the specific operations described herein when such instructions are executed.

As one particular example embodiment, the processor 202 is configured to perform various operations associated with explosion predicting, for example to generate explosion prediction data that accurately represents a likelihood of an explosion in a particular environment. In some embodiments, the processor 202 includes hardware, software, firmware, and/or a combination thereof, that receives and/or stores sensor data from one or more sensor(s) associated with an environment. Additionally or alternatively, in some embodiments, the processor 202 includes hardware, software, firmware, and/or a combination thereof, that generates a data-constructed image from received sensor data. Additionally or alternatively still, in some embodiments, the processor 202 includes hardware, software, firmware, and/or a combination thereof, that processes a data-constructed image to determine explosion contribution level(s). Additionally or alternatively still, in some embodiments, the processor 202 includes hardware, software, firmware, and/or a combination thereof, that determines whether to continue a process for explosion predicting. Additionally or alternatively still, in some embodiments, the processor 202 includes hardware, software, firmware, and/or a combination thereof, that generates explosion prediction data based at least in part on at least a portion of a data-constructed image.

In some embodiments, the apparatus 200 includes input/output circuitry 206 that provides output to the user and, in some embodiments, to receive an indication of a user input. In some embodiments, the input/output circuitry 206 is in communication with the processor 202 to provide such functionality. The input/output circuitry 206 may comprise one or more user interface(s) and in some embodiments includes a display that comprises the interface(s) rendered as a web user interface, an application user interface, a user device, a backend system, or the like. In some embodiments, the input/output circuitry 206 also includes a keyboard, a mouse, a joystick, a touch screen, touch areas, soft keys a microphone, a speaker, or other input/output mechanisms. The processor 202 and/or input/output circuitry 206 comprising the processor may be configured to control one or more functions of one or more user interface elements through computer program instructions (e.g., software and/or firmware) stored on a memory accessible to the processor (e.g., memory 204, and/or the like). In some embodiments, the input/output circuitry 206 includes or utilizes a user-facing application to provide input/output functionality to a client device and/or other display associated with a user.

In some embodiments, the apparatus 200 includes communications circuitry 208. The communications circuitry 208 includes any means such as a device or circuitry embodied in either hardware or a combination of hardware and software that is configured to receive and/or transmit data from/to a network and/or any other device, circuitry, or module in communication with the apparatus 200. In this regard, in some embodiments the communications circuitry 208 includes, for example, a network interface for enabling communications with a wired or wireless communications network. Additionally or alternatively in some embodiments, the communications circuitry 208 includes one or more network interface card(s), antenna(s), bus(es), switch(es), router(s), modem(s), and supporting hardware, firmware, and/or software, or any other device suitable for enabling communications via one or more communications network(s). Additionally or alternatively, the communications circuitry 208 includes circuitry for interacting with the antenna(s) and/or other hardware or software to cause transmission of signals via the antenna(s) or to handle receipt of signals received via the antenna(s). In some embodiments, the communications circuitry 208 enables transmission to and/or receipt of data from a client device, capture device, and/or other external computing device in communication with the apparatus 200.

The data monitoring circuitry 210 includes hardware, software, firmware, and/or a combination thereof, that supports various functionality associated with capturing, storing, receiving, and/or retrieving sensor data associated with one or more sensor(s) in a particular environment. For example, in some embodiments, the data monitoring circuitry 210 includes or is communicable with one or more sensor(s) associated with the environment, for example gas sensor(s) and/or flame sensor(s). Additionally or alternatively, in some embodiments, the data monitoring circuitry 210 includes hardware, software, firmware, and/or the like, that receives sensor data from one or more sensor(s), such as gas sensor data and/or flame sensor data. In some embodiments the apparatus 200 receives the sensor data in accordance with a particular sampling rate that the sensor is configured to capture and/or sample from the environment. Additionally or alternatively, in some embodiments, the data monitoring circuitry 210 includes hardware, software, firmware, and/or the like, that stores and/or otherwise maintains the received data for a particular sensor, for example where the sensor data is stored associated with identifier data corresponding to the sensor utilized to capture said data, optional additional data indicating a sub-region of the environment where the sensor that captured said data is located, and/or metadata associated with the captured sample. Additionally or alternatively, in some embodiments, the data monitoring circuitry 210 includes hardware, software, firmware, and/or the like, that processes received data to derive one or more data values therefrom, for example averaged value(s), changes in data value(s), and/or the like. In some embodiments, data monitoring circuitry 210 includes a separate processor, specially configured field programmable gate array (FPGA), or a specially programmed application specific integrated circuit (ASIC).

In some embodiments, the data monitoring circuitry 210 of the apparatus 200 includes the one or more sensor(s) utilized to capture sensor data from the environment. In some such embodiments, the data monitoring circuitry 210 additionally or alternatively includes hardware, software, firmware, and/or a combination thereof, that activates such sensor(s). It will be appreciated that, in some embodiments, the apparatus 200 does not perform the operations for capturing such data from processing. Instead, in some embodiments, the apparatus 200 receives the captured data for processing, for example from one or more external sensor(s). In this regard, in some embodiments the apparatus 200 does not include any such sensor(s).

The image management circuitry 212 includes hardware, software, firmware, and/or a combination thereof, that supports various functionality associated with generating and/or maintaining data-constructed image(s) for further processing as described herein. For example, in some embodiments, the image management circuitry 212 includes hardware, software, firmware, and/or any combination thereof, that generates a data-constructed image. Additionally or alternatively, in some embodiments, image management circuitry 212 includes hardware, software, firmware, and/or any combination thereof, that assigns pixel values to one or more channels of a data-constructed image based on captured data value(s) (e.g., gas sensor data and/or flame sensor data) and/or data value(s) derived therefrom. Additionally or alternatively, in some embodiments, image management circuitry 212 includes hardware, software, firmware, and/or any combination thereof, that generates a plurality of sub-images from captured data value(s). Additionally or alternatively, in some embodiments, image management circuitry 212 includes hardware, software, firmware, and/or any combination thereof, that synthesizes a plurality of sub-images to generate a data-constructed image, for example by stitching the plurality of sub-images at particular pixel sub-regions of the data-constructed image. Additionally or alternatively, in some embodiments, image management circuitry 212 includes hardware, software, firmware, and/or any combination thereof, that identify and/or extract particular portion(s) of a data-constructed image, for example pixel sub-region(s) of a data-constructed image based on particular data (e.g., explosion contribution level(s)). In some embodiments, the image management circuitry 212 includes a separate processor, specially configured field programmable gate array (FPGA), or a specially programmed application specific integrated circuit (ASIC).

The prediction processing circuitry 214 includes hardware, software, firmware, and/or a combination thereof, that supports various functionality associated with determining whether to initiate explosion predicting process(es) and/or performing such explosion predicting process(es). For example in some embodiments, the prediction processing circuitry 214 includes hardware, software, firmware, and/or a combination thereof, that applies a data-constructed image to computer vision model(s) that determine explosion contribution level(s) for one or more sub-regions of the data-constructed image. In some embodiments, the prediction processing circuitry 214 includes hardware, software, firmware, and/or a combination thereof, that applies the data-constructed image to at least one computer vision model to determine explosion contribution level(s) for one or more pixel sub-region(s) of a data-constructed image. Additionally or alternatively, in some embodiments, the prediction processing circuitry 214 includes hardware, software, firmware, and/or a combination thereof, that determine whether to initiate and/or otherwise continue an explosion predicting process based at least in part on determined explosion contribution level(s) (e.g., wherein such continuing is initiated in a circumstance where the explosion contribution level(s) satisfy a particular threshold). Additionally or alternatively, in some embodiments, the prediction processing circuitry 214 includes hardware, software, firmware, and/or a combination thereof, that generates explosion prediction data based at least in part on at least a portion of the data-constructed image. In some embodiments, the prediction processing circuitry 214 includes hardware, software, firmware, and/or a combination thereof, that applies at least a portion of the data-constructed image to at least one prediction model to generate the explosion prediction data. Additionally or alternatively, in some embodiments, the prediction processing circuitry 214 includes hardware, software, firmware, and/or a combination thereof, that generates warning signal(s) that trigger or otherwise cause outputting of alert(s) associated with the explosion prediction data. In some embodiments, the prediction processing circuitry 214 includes a separate processor, specially configured field programmable gate array (FPGA), or a specially programmed application specific integrated circuit (ASIC).

Additionally or alternatively, in some embodiments, two or more of the sets of circuitries 202-214 are combinable. Alternatively or additionally, in some embodiments, one or more of the sets of circuitry perform some or all of the functionality described associated with another component. For example, in some embodiments, two or more of the sets of circuitry 202-214 are combined into a single module embodied in hardware, software, firmware, and/or a combination thereof. Similarly, in some embodiments, one or more of the sets of circuitry, for example the data monitoring circuitry 210, the image management circuitry 212, and/or the prediction processing circuitry 214, is/are combined with the processor 202, such that the processor 202 performs one or more of the operations described above with respect to each of these sets of circuitry 210-214.

Example Generation Data-Constructed Image and Processing of the Disclosure

Having described example systems and apparatuses of the disclosure, example visualizations of generation and processing of data-constructed images will now be discussed. In some embodiments, one or more specially configured computing device(s) is configured via hardware, software, firmware, and/or any combination thereof, to perform such generation and/or processing of data-constructed images. For example, in some embodiments the explosion prediction system 108 embodied by the apparatus 200 maintains the data environments and/or performs the functionality as depicted and described with respect to FIGS. 3-6.

Figure 3:
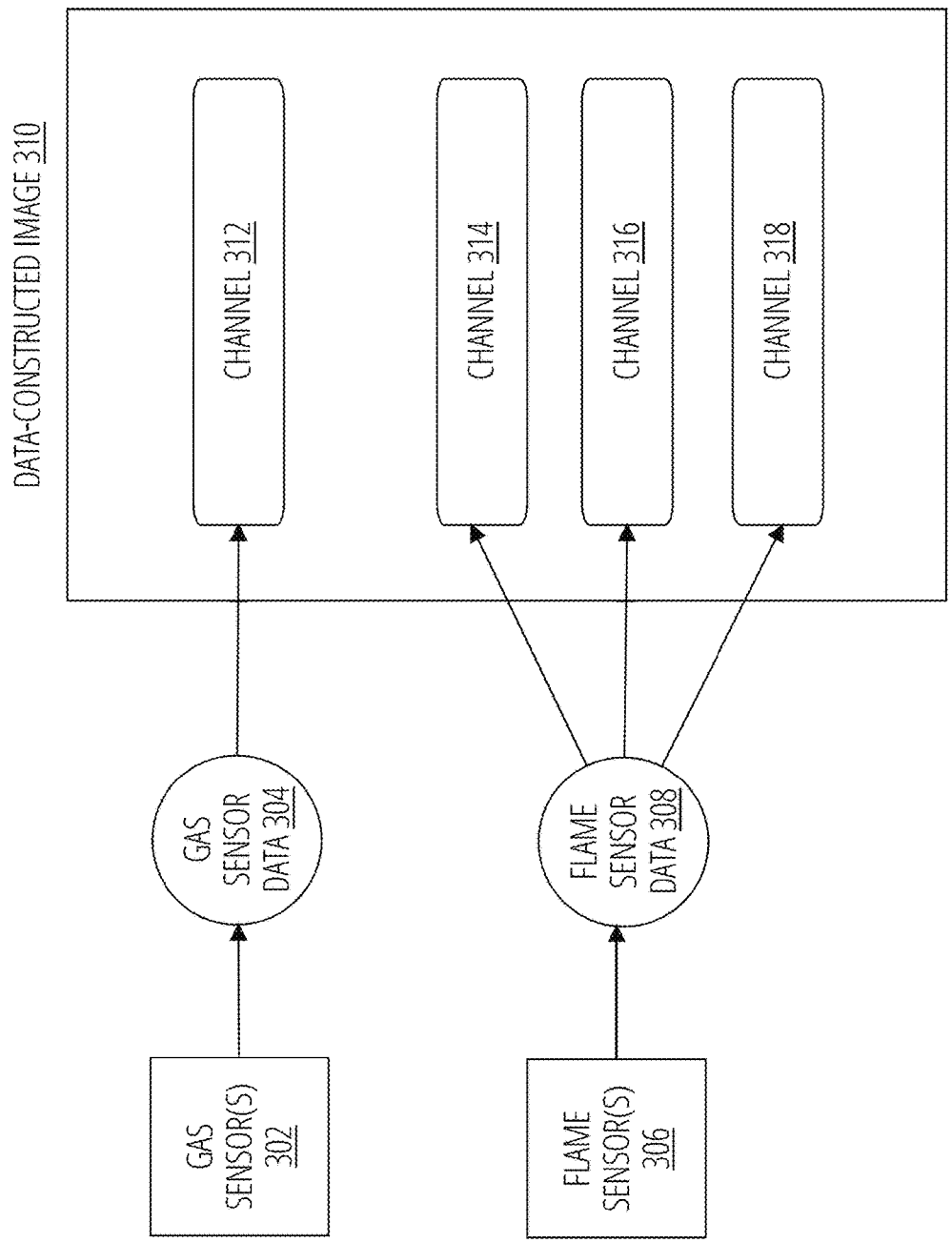
FIG. 3 illustrates an example implementation of a data-constructed image in accordance with at least some example embodiments of the present disclosure.

FIG. 3 illustrates an example implementation of a data-constructed image in accordance with at least some example embodiments of the present disclosure. FIG. 3 depicts an arrangement of data that embodies a data-constructed image, specifically a multi-channel data-constructed image 310 comprising channels 312-318. In some embodiments, the channels 312-318 correspond to RGBa channels of a particular image format. In other embodiments, it will be appreciated that the channels 312-318 may correspond to any custom format, and that a data-constructed image may be generated of any number of channels. The pixels of each of channels 312-318 are arranged based at least in part on captured sensor data, specifically gas sensor data 304 and flame sensor data 308 captured via gas sensor(s) 302 and flame sensor(s) 306 respectively. It will be appreciated that in other embodiments, the data-constructed image 310 may be embodied by an alternative arrangement of channels, for example a different number of channels and/or a different arrangement of channels. Additionally, or alternatively, in other embodiments the data-constructed image 310 is generated utilizing an alternative methodology for assigning the gas sensor data 304 and flame sensor(s) 306 to the various channels of the data-constructed image 310.

As illustrated, the gas sensor(s) 302 captures gas sensor data 304. In some embodiments, the gas sensor data 304 represents gas concentration(s), indication(s) of presence, and/or the like for one or more gas type(s). In one example context, the gas sensor data 304 includes parts-per-million concentration values for one or more gas types from samples captured from an environment. In some embodiments, the gas sensor data 304 includes a plurality of portions of gas sensor data, for example representing data value(s) determined for consecutively captured sample(s) via a gas sensor of the gas sensor(s) 302. In some embodiments, the gas sensor data 304 includes averaged values for the plurality of gas sensor data portions, for example, such that multiple data value(s) for consecutive samples captured at a first sampling rate are averaged (e.g., with a simple or weighted average) or otherwise manipulated to be associated with a second sampling rate. In a circumstance where the gas sensor(s) 302 capture at a sampling rate of 8 ms for example, and the gas sensor data 304 is to be processed at a 16 ms sampling rate, two consecutive data value(s) may be averaged to determine one portion of the gas sensor data 304. Additionally or alternatively, in some embodiments the gas sensor data 304 includes portions of gas sensor data captured via a plurality of gas sensor(s) 302 positioned at different locations in an environment, for example within different sub-regions.

As illustrated, the flame sensor(s) 306 captures flame sensor data 308. In some embodiments, the flame sensor data 308 includes data values indicating whether a flame is present at a particular sub-region in the environment. In one example context, the flame sensor data 308 includes data for a plurality of bands measured via the flame sensor(s) 306, for example near-band, wide-band, and/or long-band infrared data sampled via the flame sensor(s) 306. In some such embodiments, each portion of flame sensor data in the flame sensor data 308 includes a plurality of data value(s), for example a near-band data value, a wide-band data value, and/or a long-band data value. In some embodiments, the flame sensor data 308 includes averaged values for a plurality of flame sensor data portions, for example, such that multiple data value(s) for consecutive samples captured at a first sampling rate are averaged (e.g., with a simple or weighted average) or otherwise manipulated to be associated with a second sampling rate. For example, in a circumstance where the flame sensor(s) 306 captures at a sampling rate of 8 ms, and the flame sensor data 308 is to be processed at a 16 ms sampling rate, two consecutive data value(s) may be averaged to determine one portion of the flame sensor data 308. Additionally or alternatively, in some embodiments, the flame sensor data 308 includes portions of flame sensor data captured via a plurality of flame sensor(s)s 306 positioned at different locations in an environment, for example within different sub-regions.

In some embodiments, the apparatus 200, for example, generates the data-constructed image 310 based at least in part on the gas sensor data 304 and flame sensor data 308. For example, in some embodiments the apparatus 200 assigns particular pixel values of the various channels of the data-constructed image 310 based at least in part on particular data of the gas sensor data 304 and/or flame sensor data 308, and/or data derived therefrom. In some embodiments, the apparatus 200 assigns a pixel value of a first channel, such as the channel 312, based at least in part on the data values of the gas sensor data 304. In some embodiments, the apparatus 200 derives a pixel value utilizing a particular algorithm that processes the concentration(s) and/or other data value(s) represented in a portion of gas sensor data, for example to weight particular gas types differently based on their likelihood to contribute to an explosion. In some embodiments, particular gas types that are more likely to contribute to an explosion are assigned a higher weight than the gas types that are less likely to contribute to an explosion, such that a single pixel value is determinable by averaging the concentrations of the gas sensor data utilizing the weights for each corresponding gas type. In this regard, the apparatus 200 may utilize portions of gas sensor data captured by a particular gas sensor of the gas sensor(s) 302 to assign subsequent pixel values of the channel 312 until the channel is fully assigned. Alternatively or additionally, in some embodiments the apparatus 200 averages data values from the gas sensor data 304 to derive a pixel value for a particular pixel, for example by averaging portions of gas sensor data 304 that are captured by a gas sensor over multiple samples, and/or that average portions of gas sensor data 304 captured by a plurality of gas sensors that are all associated with the same sub-region of an environment. In some embodiments, pixels of the channel 312 are arranged sequentially (e.g., starting from a (0, 0) pixel coordinate) to fill the channel 312 and/or a portion thereof.

In some embodiments, different portions of the gas sensor data 304 are utilized to assign pixel(s) at different pixel sub-regions of the channel 312. For example, in some embodiments, a first portion of the gas sensor data 304 captured via gas sensor(s) of the gas sensor(s) 302 from a first sub-region of the environment are utilized to assign pixels of a first pixel sub-region corresponding to the first sub-region of the environment, a second portion of the gas sensor data 304 captured via gas sensor(s) of the gas sensor(s) 302 from a second sub-region of the environment are utilized to assign pixels of a second pixel sub-region corresponding to the second sub-region of the environment, and/or the like for any number of sub-regions.

The remaining channels channel 314, 316, and 318 may similarly be assigned based on the data value(s) of the flame sensor data 308. In some embodiments, the apparatus 200 assigns pixel values of a plurality of channels based at least in part on data values for the different frequency bands for each portion of the flame sensor data 308. In some embodiments, the apparatus 200 assigns a pixel value of a second channel, such as the channel 314, based at least in part on data values for a first band of the flame sensor data 308, assigns a pixel value of a third channel, such as the channel 316, based at least in part on data values for a second band of the flame sensor data 308, and assigns a pixel value of a fourth channel, such as the channel 318, based at least in part on data values for a third band of the flame sensor data 308. In one example context, the apparatus 200 assigns pixel values for channel 314 based at least in part on near-band data values of an IR reading via a flame sensor of the flame sensor(s) 306, assigns pixel values for channel 316 based at least in part on wide-band data values of the IR reading via the flame sensor of the flame sensor(s) 306, and assigns pixel values for channel 318 based at least in part on long-band data values of the IR reading via the flame sensor of the flame sensor(s) 306. In some embodiments, the apparatus 200 derives a pixel value for each of the channels utilizing a particular algorithm that processes the data value for the band corresponding to the channel. In this regard, the apparatus 200 may utilize portions of flame sensor data captured by a particular flame sensor of the flame sensor(s) 306 to assign subsequent pixel values of any one of the channels 314, 316, and/or 318, until the channel is fully assigned. Alternatively or additionally, in some embodiments the apparatus 200 averages data values from the flame sensor data 308 to derive a pixel value for a particular pixel, for example by averaging portions of flame sensor data 308 that are captured by a gas sensor over multiple samples, and/or that average portions of flame sensor data 308 captured by a plurality of flame sensors that are all associated with the same sub-region of an environment. In some embodiments, pixels of the channel 314, 316, and/or 318 are arranged sequentially (e.g., starting from a (0, 0) pixel coordinate) to fill the channel and/or a portion thereof.

It will be appreciated that in other embodiments, the gas sensor data and/or flame sensor data is utilized to generate and/or otherwise assign data to any other number of channels. For example, in some embodiments, different portions of gas sensor data (e.g., associated with different gas types) is utilized to assign pixel values to a plurality of channels. Alternatively or additionally, in some embodiments flame sensor data is utilized to assign only a single channel, or a different number of channels (e.g., two channels, four or more channels, and/or the like). It will be appreciated that the channels available and/or utilized for processing via the data-constructed image may be generated as available and/or as needed. In this regard, the particular depicted example data-constructed image should not limit the scope or spirit of this disclosure.

Figure 4:
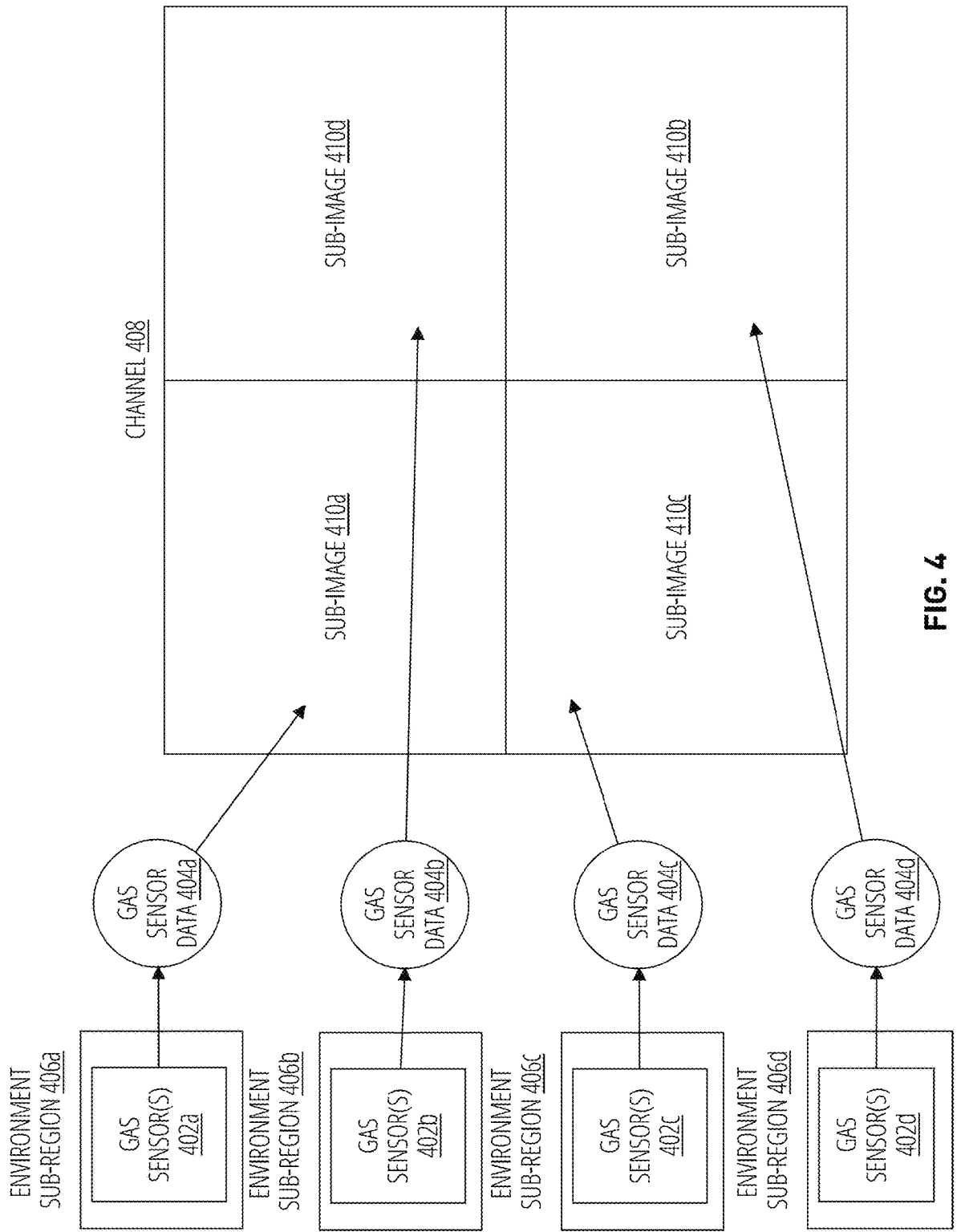
FIG. 4 illustrates a visualization of an example process for constructing a channel from a plurality of sub-images in accordance with at least some example embodiments of the present disclosure.

FIG. 4 illustrates a visualization of an example process for constructing a channel from a plurality of sub-images in accordance with at least some example embodiments of the present disclosure. It should be appreciated that any of the channels 312-318 may be generated as described with respect to FIG. 4. In some embodiments, all channels of a particular image are generated utilizing the sub-imaging method as depicted and described herein. In some other embodiments, only some channels of the particular image are generated utilizing the sub-imaging method as depicted and described herein. Additionally, though a channel is depicted as being generated utilizing gas sensor data, it will be appreciated that the sub-imaging method described herein may similarly be utilized to generate one or more channel(s) based at least in part on flame sensor data.

In some embodiments, a particular environment includes a plurality of sub-regions. For example, in some embodiments, an environment includes a plurality of sub-regions defining different rooms of the environment, different areas separated by a particular distance, different areas separated by particular physical element(s), and/or the like. It will be appreciated that an environment may be sub-divided into any number of sub-regions, which may be of the same size or of different sizes.

As illustrated, each sub-region of a plurality of sub-regions for a particular environment each include one or more gas sensor(s). For example, the environment sub-region 406a is associated with gas sensor(s) 402a, environment sub-region 406b is associated with gas sensor(s) 402b, environment sub-region 406c is associated with gas sensor(s) 402c, and environment sub-region 406d is associated with environment sub-region 406d. In some embodiments, each gas sensor of the gas sensor(s) 402a-402d is located within its corresponding sub-region of the environment. Additionally or alternatively, in some embodiments the apparatus 200 maintains data indicating the association between a particular gas sensor and its corresponding sub-region of the environment, such that gas sensor data received from the corresponding gas sensor may be processed associated with a particular sub-region of the environment. In some embodiments, the apparatus 200 stores data associating an identifier a particular gas sensor with a data identifier identifying the corresponding sub-region of the environment.

As illustrated, each of the gas sensor(s) captures one or more portions of gas sensor data. For example, in some embodiments gas sensor(s) 402a captures gas sensor data 404a, which is associated with environment sub-region 406a. Similarly, gas sensor(s) 402b captures 404b, which is associated with environment sub-region 406b, and so on. In some such embodiments, the apparatus 200 associates each of the gas sensor data 404a, gas sensor data 404b, gas sensor data 404c, and gas sensor data 404d with the corresponding sub-region of the environment based at least in part on one or more data identifier(s), for example identifying the sensor that captured the particular portion of gas sensor data. In this regard, the apparatus 200 may maintain such portions of gas sensor data with the corresponding environment sub-regions for further processing.

The apparatus 200 generates a plurality of sub-images based on the different sets of gas sensor data. For example, in some embodiments, the apparatus 200 generates a sub-image for each region of the environment for which data was captured. As illustrated, the apparatus 200 generates a first sub-image 410a corresponding to the environment sub-region 406a, a second sub-image 410b corresponding to environment sub-region 406b, a third sub-image 410c corresponding to environment sub-region 406c, and a fourth sub-image 410d corresponding to environment sub-region 406d. Each of the sub-images may be generated based on the set of gas sensor data corresponding to that particular sub-region of the environment, for example the gas sensor data 404a corresponding to sub-image 410a, gas sensor data 404b corresponding to sub-image 410b, gas sensor data 404c corresponding to sub-image 410c, and gas sensor data 404d corresponding to sub-image 410d.

It should be appreciated that the pixels of any particular sub-image may be assigned as described above with respect to FIG. 3. For example, the pixel values of the sub-image 410a may be assigned sequentially based at least in part on the data values of the corresponding gas sensor data 404a, or data value(s) derived therefrom. Pixel values may be assigned to each pixel of the sub-images until each sub-image is filled. For example, the pixel values of the sub-image 410b may be assigned sequentially based at least in part on the data values of the corresponding gas sensor data 404b, and so on.

In some embodiments, the apparatus 200 generates the channel 408 based at least in part on the plurality of sub-images once assignment of the pixel values for such sub-images are complete. In this regard, in some embodiments each sub-image corresponds to a pixel sub-region of the channel 408. In some embodiments, the pixel sub-region corresponding to a particular sub-region is predetermined, for example based at least in part on the corresponding sub-region of an environment corresponding to that sub-image. For example, as illustrated, the sub-image 410a corresponds to a top-left pixel sub-region of the channel 408, sub-image 410b corresponds to a bottom-right pixel sub-region of the channel 408, sub-image 410c corresponds to a bottom-left pixel sub-region of the channel 408, and sub-image 410d corresponds to a top-right pixel sub-region of the channel 408. In some embodiments, the apparatus 200 stitches the various sub-images in alignment with each sub-image's corresponding pixel sub-region. In this regard, the resulting channel 408 includes all pixel values for all sub-regions.

Such generation of a channel image utilizing sub-images may be repeated for any number of channels. For example, in some embodiments the apparatus 200 repeats the process for generating a plurality of channels utilizing different data, for example gas sensor data for a first channel, a first portion of flame sensor data for a second channel, a second portion of the flame sensor data for a third channel, and a third portion of flame sensor data for a fourth channel. Additionally or alternatively, in some embodiments, the apparatus 200 generates a data-constructed image by layering the channels upon completion of generating of each channel image.

Figure 5:
FIG. 5 illustrates an example data-constructed image in accordance with at least some example embodiments of the present disclosure.

FIG. 5 illustrates an example data-constructed image in accordance with at least some example embodiments of the present disclosure. Specifically, FIG. 5 depicts an example data-constructed image 500. In some embodiments, the data-constructed image 500 includes a plurality of pixel sub-region, for example corresponding to different sub-regions of a particular environment represented by the data-constructed image 500.

As illustrated, the pixels of the data-constructed image 500 may be represented by the pixel values of each channel of the data-constructed image 500. In one example context, for example where the data-constructed image 500 is represented in RGBa format, each pixel is depicted in the data-constructed image 500 as a color value having a particular transparency, for example determined based on the pixel value at each channel. In some embodiments, for example where the pixel values are assigned as subsequent samples are captured via one or more sensor(s), the data-constructed image 500 may depict changes in the data values measured via the captured samples. In this regard, the data-constructed image 500 may represent a rate of change of the measured value corresponding to such sensors.

It will be appreciated that the data-constructed image 500 may be represented in a known image format (e.g., RGBa as described herein). In this regard, the data-constructed image 500 may advantageously be processed in any of a myriad of known manners utilized to process such images. For example, in some embodiments, known image processing algorithms, machine learning models, and/or the like may be utilized to process the data-constructed image 500, and/or specially-configured algorithms, machine learning models, and/or the like may be utilized, as described further herein. Additionally or alternatively, the data-constructed image 500 may be outputted for displaying via one or more user interface(s). In some embodiments, the data-constructed image is not processable in a manner readily interpretable by a user and/or renderable via one or more user interface(s), for example where the data-constructed image includes more channels than known image formats readily interpret.

Figure 6:
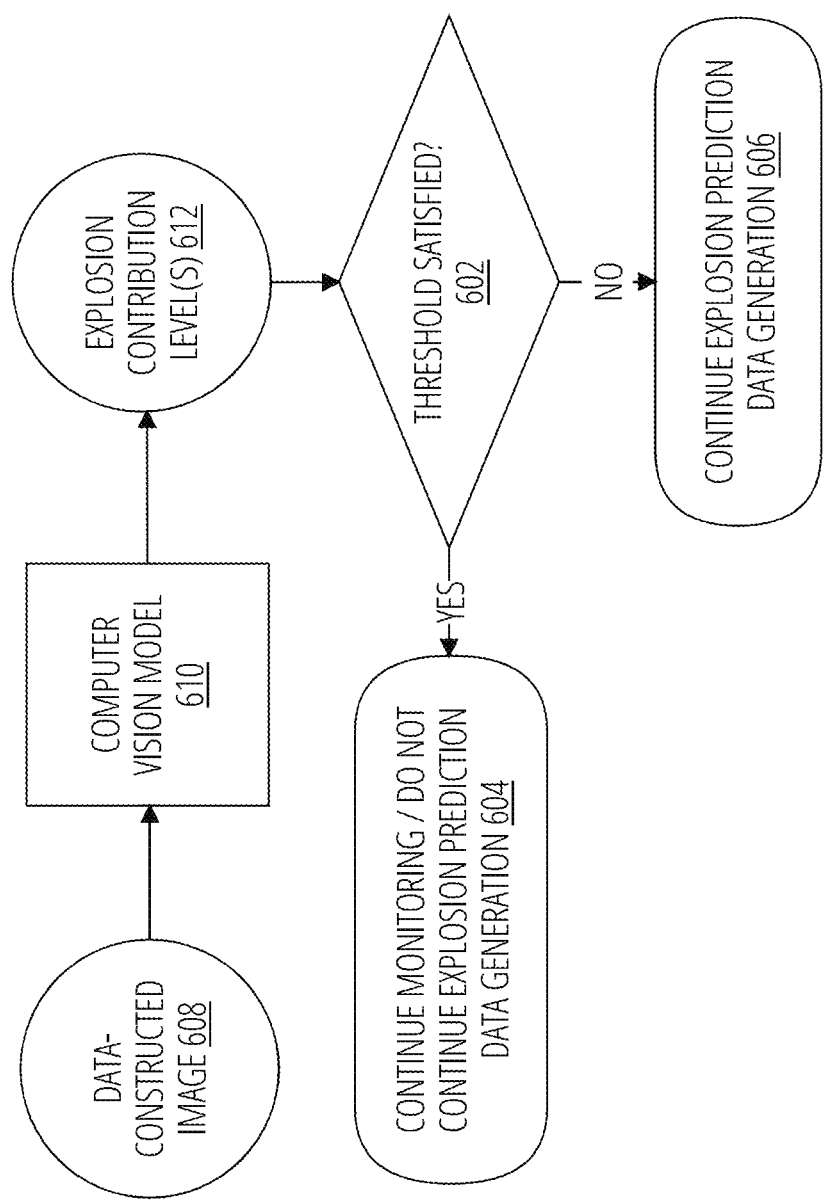
FIG. 6 illustrates an example data flow for determining whether to initiate explosion prediction data generation in accordance with at least some embodiments of the present disclosure.

FIG. 6 illustrates an example data flow for determining whether to initiate explosion prediction data generation in accordance with at least some embodiments of the present disclosure. In some embodiments, the apparatus 200 processes data in accordance with the data flow depicted and described. The apparatus 200 may perform such a data flow alone or in combination with one or more other device(s), including one or more user device(s), sensor(s), and/or the like.

As illustrated, the apparatus 200 (for example), retrieves, maintains, and/or otherwise includes the data-constructed image 608. In some embodiments, the apparatus 200 generates the data-constructed image 608 as depicted and described herein, for example with respect to FIGS. 3-5.

In some embodiments, the apparatus 200 applies the data-constructed image 608 to a computer vision model 610. In some embodiments, the computer vision model 610 embodies a specially trained machine-learning model and/or AI model that processes image data, for example image data in the format of the data-constructed image 608. For example, in some embodiments the computer vision model 610 is trained such that the model learns the features of each image that correspond to each explosion contribution level, as described further herein. In some embodiments, the computer vision model 610 embodies a machine-learning model trained utilizing a supervised learning method or unsupervised learning method. In some embodiments, the computer vision model 610 is specially trained to extract particular explosion feature data from inputted image data. In this regard, in some embodiments the computer vision model 610 is specially trained to generate particular output based at least in part on the explosion feature data.

As illustrated, the computer vision model 610 outputs explosion contribution level(s) 612. In some embodiments, the explosion contribution level(s) 612 includes data values indicating whether particular explosion contributing factor(s) were sufficiently detected from the data-constructed image 608. In some embodiments, the computer vision model 610 outputs explosion contribution level(s) 612 indicating a selected level from a plurality of candidate explosion contribution levels. In one example context, the computer vision model 610 outputs a selected explosion contribution level from a plurality of candidate explosion contribution levels including a first explosion contribution level indicating a normal or ambient environment (e.g., with no detected explosion contributing factors or less than a particular threshold), a second explosion contribution level indicating a gas leak is detected (e.g., gas concentration(s) above a particular threshold), and/or a third explosion contribution level indicating a flame or sufficient heat energy for explosion is detected (e.g., heat or flame indications above a particular threshold). In some embodiments, the explosion contribution levels are tiered, such that a third explosion contribution level requires all factors of a previous second explosion contribution level (e.g., where the second explosion contribution level represents presence of a gas leak, and the third explosion contribution level represents presence of a gas leak and heat energy or flame).

In some embodiments, the computer vision model 610 generates an explosion contribution level for different portions of the data-constructed image 608. For example, in some embodiments, the computer vision model 610 generates an independent explosion contribution level for each pixel sub-region of the data-constructed image 608. In this regard, the computer vision model 610 may indicate the particular pixel sub-regions that are associated with a risk of explosion, as represented the explosion contribution level(s) 612. Similarly, based on the explosion contribution level of the explosion contribution level(s) 612 for each of the pixel sub-regions, the corresponding sub-regions of the environment represented by the data-constructed image 608 may be identified based on such explosion contribution level(s) 612 and associations between the pixel sub-regions and sub-regions of the environment. In some such contexts, the identification of sub-regions of an environment particularly at risk for explosion enables processing to be focused only on data associated with such sub-regions in particular, for example in the subsequent operations as described herein.

In some embodiments, the apparatus 200 determines whether to continue a process for explosion predicting based at least in part on the explosion contribution level(s) 612. For example in some embodiments, the apparatus 200 determines whether each of the explosion contribution level(s) 612 satisfies a particular threshold. In some embodiments, the apparatus 200 the threshold indicates a maximum level indicating that a particular environment (or sub-region thereof) is sufficiently not at risk of explosion. For example, in the example context where the explosion contribution level(s) 612 are each selected from a first explosion contribution level indicating a normal or ambient environment, a second explosion contribution level indicating a gas leak is detected, and/or a third explosion contribution level indicating a flame or sufficient heat energy for explosion is detected, the threshold may indicate that only the first explosion contribution level indicating normal ambient conditions is sufficient to cease the processes for explosion predicting.

In this regard, the apparatus 200 may compare the explosion contribution level from explosion contribution level(s) 612 for the environment, or individual pixel sub-regions thereof, with the threshold to determine whether the threshold is exceeded (e.g., whether the explosion contribution level is other than a normal level, in one example context). In circumstances where the apparatus 200 determines the threshold is satisfied (e.g., the level for a particular sub-region is normal), the apparatus 200 may proceed to perform block 604. At block 604, the apparatus 200 may continue monitoring for sensor data, but does not continue explosion prediction data generation for the environment and/or particular sub-region of the environment. In this regard, the apparatus 200 may forego further processing of the data associated with the particular corresponding sub-regions until subsequent data indicates a change in the corresponding explosion contribution level that satisfies the threshold at decision block 602. In circumstances where the apparatus 200 determines the threshold is not satisfied (e.g., the level for a particular sub-region is not normal or otherwise above another threshold), the apparatus 200 may proceed to perform block 606. At block 606, the apparatus 200 continues explosion prediction data generation for the environment, or at least the sub-region corresponding to the explosion contribution level that satisfied the threshold. For example, in some embodiments the apparatus 200 generates the explosion prediction data for one or more sub-regions by applying at least a portion of the data-constructed image 608 to a prediction model as described further herein.

It should be appreciated that the process described herein for receiving sensor data, processing sensor data to generate a data-constructed image, and processing the data-constructed image to determine whether to continue explosion prediction data generation may be repeated any number of times. In this regard, the apparatus 200, for example, may continually perform such a process to continually monitor a particular environment and detect when the environment, or particular sub-regions thereof, may be at risk of explosion. Such determinations as depicted and described with respect to FIG. 6 advantageously prevent unnecessary waste of computing resources for processing data associated with an environment or sub-region thereof in circumstances where particular explosion contributing factors for explosion are not determined sufficiently present with reduced processing.

Example Processes of the Disclosure

Having described example systems and apparatuses, data-constructed images and related data flows in accordance with the disclosure, example processes of the disclosure will now be discussed. It will be appreciated that each of the flowcharts depicts an example computer-implemented process that is performable by one or more of the apparatuses, systems, devices, and/or computer program products described herein, for example utilizing one or more of the specially configured components thereof.

The blocks indicate operations of each process. Such operations may be performed in any of a number of ways, including, without limitation, in the order and manner as depicted and described herein. In some embodiments, one or more blocks of any of the processes described herein occur in-between one or more blocks of another process, before one or more blocks of another process, in parallel with one or more blocks of another process, and/or as a sub-process of a second process. Additionally or alternatively, any of the processes in various embodiments include some or all operational steps described and/or depicted, including one or more optional blocks in some embodiments. With regard to the flowcharts illustrated herein, one or more of the depicted block(s) in some embodiments is/are optional in some, or all, embodiments of the disclosure. Optional blocks are depicted with broken (or "dashed") lines. Similarly, it should be appreciated that one or more of the operations of each flowchart may be combinable, replaceable, and/or otherwise altered as described herein.

Figure 7:
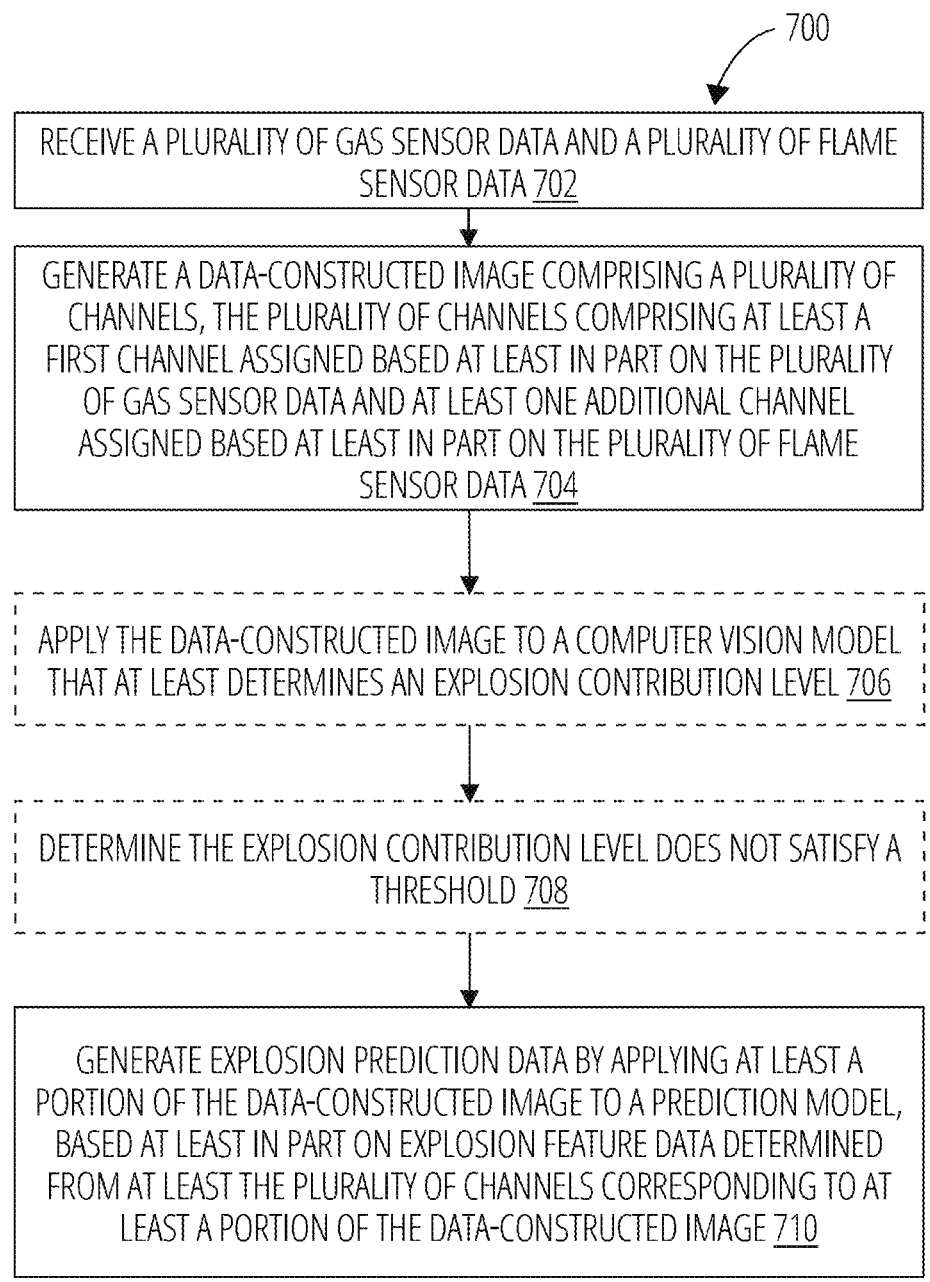
FIG. 7 illustrates a process 700 for generating explosion prediction data in accordance with at least some example embodiments of the present disclosure.

FIG. 7 illustrates a process 700 for generating explosion prediction data in accordance with at least some example embodiments of the present disclosure. In some embodiments, the process 700 is embodied by computer program code stored on a non-transitory computer-readable storage medium of a computer program product configured for execution to perform the process as depicted and described. Alternatively or additionally, in some embodiments, the process 700 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with an end-user computing device, sensor(s), alert system(s), and/or the like. For purposes of simplifying the description, the process 700 is described as performed by and from the perspective of the apparatus 200.

The process 700 begins at operation 702. In operation 702, process 700 receives a plurality of gas sensor data and a plurality of flame sensor data. The plurality of gas sensor data may include any number of gas sensor data portions captured from an environment, and/or the plurality of flame sensor data may include any number of flame sensor data portions captured from the environment. In some embodiments, the apparatus 200 receives the gas sensor data from one or more gas sensor(s) in an environment, and/or receives the flame sensor data from one or more flame sensor(s) in an environment. In some embodiments, different portions of the plurality of gas sensor data are associated with different sub-regions of an environment, and/or different portions of the plurality of flame sensor data are associated with different sub-regions of an environment. In some such embodiments, the different portions are associated with different sub-regions based at least in part on data indicating the sensor that captured such data.

In operation 704, process 700 generates a data-constructed image comprising a plurality of channels, the plurality of channels comprising at least a first channel assigned based at least in part on the plurality of gas sensor data and at least one additional channel assigned based at least in part on the plurality of flame sensor data. In some embodiments, the apparatus 200 for example assigns a first channel based at least in part on the gas concentration values of the plurality of gas sensor data, and assigns a second channel, third channel, and fourth channel of the additional channels based at least in part on different bands of data represented in each portion of the plurality of flame sensor data. In some embodiments, the apparatus 200 generates the data-constructed image by generating a plurality of sub-images, for example associated with different sub-regions of an environment, and combining or otherwise stitching such sub-images together in accordance with defined pixel sub-regions corresponding to each sub-image. In some embodiments, the pixel sub-regions are predefined, such that pixels in particular pixel sub-regions are always assigned based on data captured from the same sensors.

In optional operation 706, process 700 applies the data-constructed image to a computer vision model that at least determines an explosion contribution level. In some embodiments, the computer vision model comprises a specially trained deep-learning, AI, or other machine-learning, statistical, or algorithmic model that is trained to determine explosion feature data from the data-constructed image and utilizes such explosion feature data to output one or more explosion contribution level(s). In some embodiments, an explosion contribution level is output corresponding to predefined pixel sub-regions of the data-constructed image, for example corresponding to particular sub-regions of a corresponding environment. Alternatively or additionally, in some embodiments, the computer vision model defines the particular pixel sub-region of the data-constructed image that is associated with a non-normal explosion contribution level.

In optional operation 708, process 700 determines that the explosion contribution level does not satisfy a threshold. For example, in some embodiments, the apparatus 200 compares the determined explosion contribution level with a threshold explosion contribution level indicating normal, such that the threshold is satisfied in circumstances where the determined explosion contribution level matches the threshold explosion contribution level. Alternatively or additionally, in some embodiments, the apparatus 200 determines the threshold is not satisfied in a circumstance where the determined explosion contribution level is not the same as the threshold explosion contribution level (e.g., not normal). It will be appreciated that in some embodiments, a plurality of explosion contribution levels corresponding to a plurality of portions of the data-constructed image are compared to the threshold, and processing continues utilizing only those portions that are determined not to satisfy the threshold.

In operation 710, process 700 generates explosion prediction data by applying at least a portion of the data-constructed image to a prediction model. In some embodiments, the prediction model comprises a specially-trained machine-learning model, AI, algorithmic, and/or statistical model that generates explosion prediction data based at least in part on input data. In some embodiments, the prediction model receives image data as input, for example at least a portion of a data-constructed image. The prediction model may then process all channels of the inputted image data to generate the corresponding explosion prediction data as output. In some embodiments, the apparatus 200 extracts particular portions of the data-constructed image that are associated with an explosion contribution level that does not satisfy the threshold (e.g., pixel sub-regions that are associated with a non-normal explosion contribution level). The extracted portions of the data-constructed image may subsequently be provided as input to the prediction model.

It should be appreciated that the prediction model may be specially trained to output any of a myriad of output types. In some embodiments, the explosion prediction data embodies a probability indicating a likelihood of explosion in an environment or a particular sub-region thereof. Alternatively or additionally, in some embodiments the explosion prediction data embodies data indicating a Boolean value of whether an explosion in the environment or a particular sub-region thereof is determined sufficiently likely.

Figure 8:
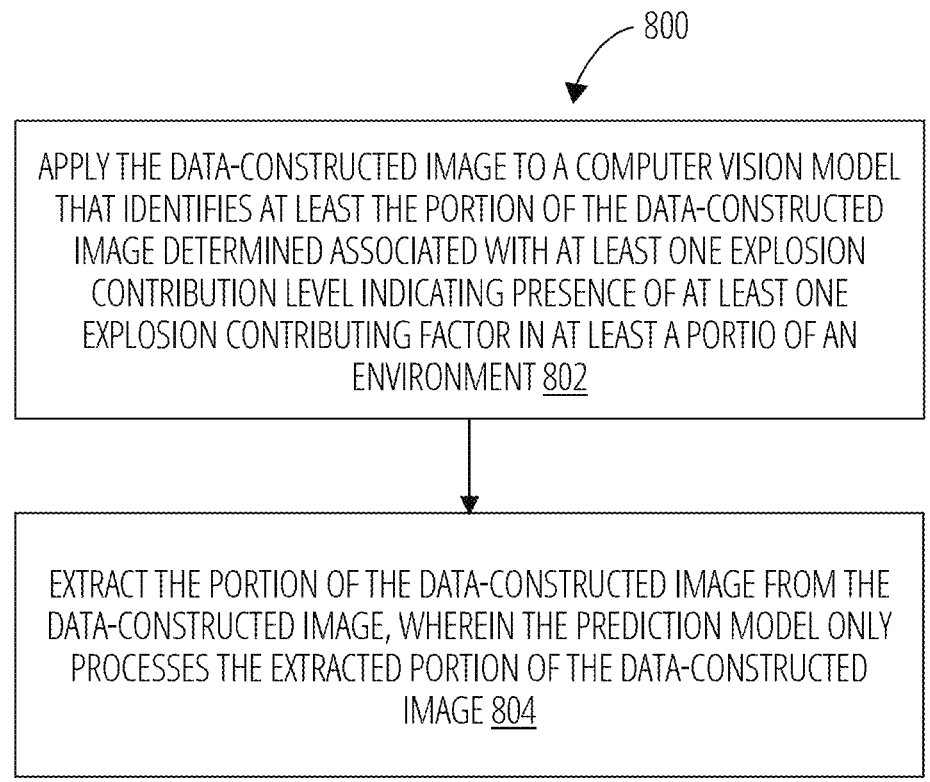
FIG. 8 illustrates a process 800 for extracting at least a portion of a data-constructed image by using a computer vision model in accordance with at least some example embodiments of the present disclosure.

FIG. 8 illustrates a process 800 for extracting at least a portion of a data-constructed image by using a computer vision model in accordance with at least some example embodiments of the present disclosure. In some embodiments, the process 800 is embodied by computer program code stored on a non-transitory computer-readable storage medium of a computer program product configured for execution to perform the process as depicted and described. Alternatively or additionally, in some embodiments, the process 800 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with an end-user computing device, sensor(s), alert system(s), and/or the like. For purposes of simplifying the description, the process 800 is described as performed by and from the perspective of the apparatus 200.

The process 800 begins at operation 802. In some embodiments, the process 800 begins after one or more operations depicted and/or described with respect to any one of the other processes described herein. For example, in some embodiments as depicted, the process 800 begins after execution of operation 704. In this regard, some or all of the process 800 may replace or supplement one or more blocks depicted and/or described with respect to any of the processes described herein. Upon completion of the process 800, the flow of operations may terminate. Additionally or alternatively, as depicted, upon completion of the process 800 in some embodiments, flow may return to one or more operation(s) of another process, such as the operation 706. It will be appreciated that, in some embodiments, the process 800 embodies a sub-process of one or more other process(es) depicted and/or described herein, for example the process 700.

In operation 802, the process 800 applies the data-constructed image to a computer vision model that identifies at least the portion of the data-constructed image determined associated with at least one explosion contribution level indicating presence of at least one explosion contributing factor in at least a portion of an environment. In some embodiments, for example, the apparatus 200 utilizes the computer vision model to process different pixel sub-regions of the data-constructed image, and determine the pixel sub-regions comprising at least one pixel associated with an identified feature in the image that indicates presence of at least one explosion contributing factor. In some embodiments, the apparatus 200 identifies pixel sub-regions from a predetermined set of defined pixel sub-regions. In other embodiments, the apparatus 200 utilizes the computer vision model to identify the particular pixels that define a pixel sub-region.

In operation 804, the process 800 extracts the portion of the data-constructed image from the data-constructed image, where the prediction model only processes the extracted portion of the data-constructed image. The computer vision model may process the data-constructed image as a whole and in some embodiments extracts all defined pixel sub-regions corresponding to at least one identified feature in the data-constructed image. In some embodiments, the apparatus 200 extracts all portions of the data-constructed image that are associated with an explosion contribution level that does not satisfy a threshold. Alternatively or additionally, in some embodiments, the apparatus 200 extracts particular pixels identified by the computer vision model as associated with a particular feature, for example indicating presence of at least one explosion contributing factor. Alternatively or additionally, in some embodiments, the apparatus 200 extracts one or more portion(s) of the data-constructed image that are not associated with an explosion contribution level that does satisfy a threshold (e.g., indicating no explosion contribution factor is detected in that region) in a circumstance where a neighboring region includes data at or near (e.g., within a relevant distance threshold as defined by a number of pixels, for example) the neighboring region. It will be appreciated that in some embodiments, the pixel sub-regions extracted from the data-constructed image is/are stored to a new image data object, file, and/or the like.

In some embodiments, the extracted portions of the data-constructed image are subsequently processed by the apparatus 200. For example, in some embodiments, only the extracted portions are inputted as the at least a portion of the data-constructed image to the prediction model, as described herein with respect to operation 708.

Figure 9:
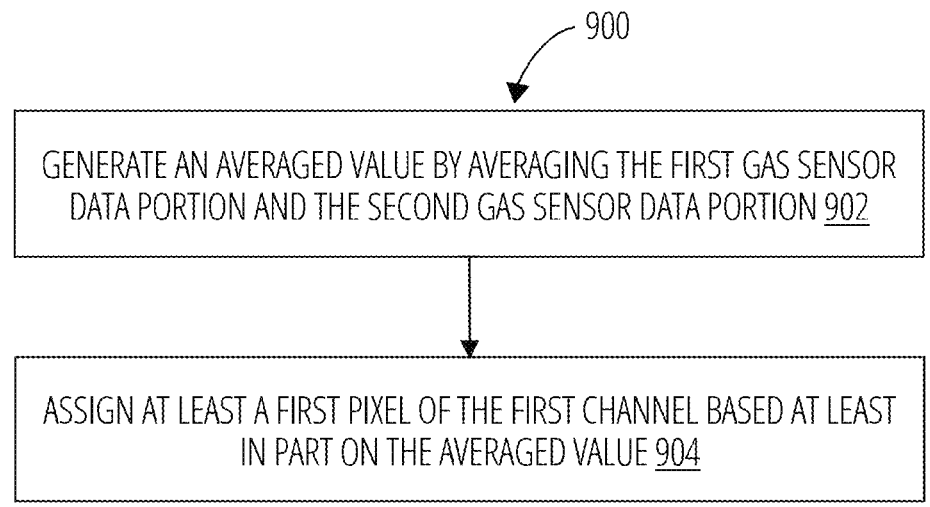
FIG. 9 illustrates a process 900 for assigning a pixel value based on an averaged value of gas sensor data in accordance with at least some example embodiments of the present disclosure.

FIG. 9 illustrates a process 900 for assigning a pixel value based on an averaged value of gas sensor data in accordance with at least some example embodiments of the present disclosure. In some embodiments, the process 900 is embodied by computer program code stored on a non-transitory computer-readable storage medium of a computer program product configured for execution to perform the process as depicted and described. Alternatively or additionally, in some embodiments, the process 900 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with an end-user computing device, sensor(s), alert system(s), and/or the like. For purposes of simplifying the description, the process 800 is described as performed by and from the perspective of the apparatus 200.

The process 900 begins at operation 902. In some embodiments, the process 900 begins after one or more operations depicted and/or described with respect to any one of the other processes described herein. For example, in some embodiments as depicted, the process 900 begins after execution of operation 702. In this regard, some or all of the process 900 may replace or supplement one or more blocks depicted and/or described with respect to any of the processes described herein. Upon completion of the process 900, the flow of operations may terminate. Additionally or alternatively, as depicted, upon completion of the process 900 in some embodiments, flow may return to one or more operation(s) of another process, such as the operation 704. It will be appreciated that, in some embodiments, the process 900 embodies a sub-process of one or more other process(es) depicted and/or described herein, for example the process 700.

In operation 902, the process 900 generates an averaged value. In some embodiments, the apparatus 200 generates the averaged value by averaging the first gas sensor data portion and the second gas sensor data portion. In some embodiments, the averaged value comprises a simple average of a plurality of gas sensor data portions, including at least the first gas sensor data portion and the second gas sensor data portion. Alternatively or additionally, in some embodiments, the averaged value comprises a weighted average of a plurality of gas sensor data portions, including at least the first gas sensor data portion and the second gas sensor data portion.

In some embodiments, the first gas sensor data portion and the second gas sensor data portion correspond to sequentially captured samples. For example, the second gas sensor data portion may be captured after the first gas sensor data portion by a particular gas sensor. In some such contexts, the averaged value may be generated corresponding to a different sampling rate than the sampling rates corresponding to individual first and second gas sensor data portions. Alternatively or additionally, in some embodiments, the first gas sensor data portion and the second gas sensor data portion are captured by different gas sensors associated with the same environment or sub-region of the environment. In some such embodiments, all gas sensor data portions from gas sensors corresponding to the sub-region may be averaged to determine a value for the sub-region associated with a particular sampling time (e.g., corresponding to samples captured at the same timestamp or within a particular interval from one another).

In operation 904, the process 900 assigns at least a first pixel of the first channel based at least in part on the averaged value. In some embodiments, for example, the pixel is assigned to the averaged value in a particular channel. In some embodiments, the first channel is predetermined (e.g., representing a particular channel corresponding to gas sensor data).

Figure 10:
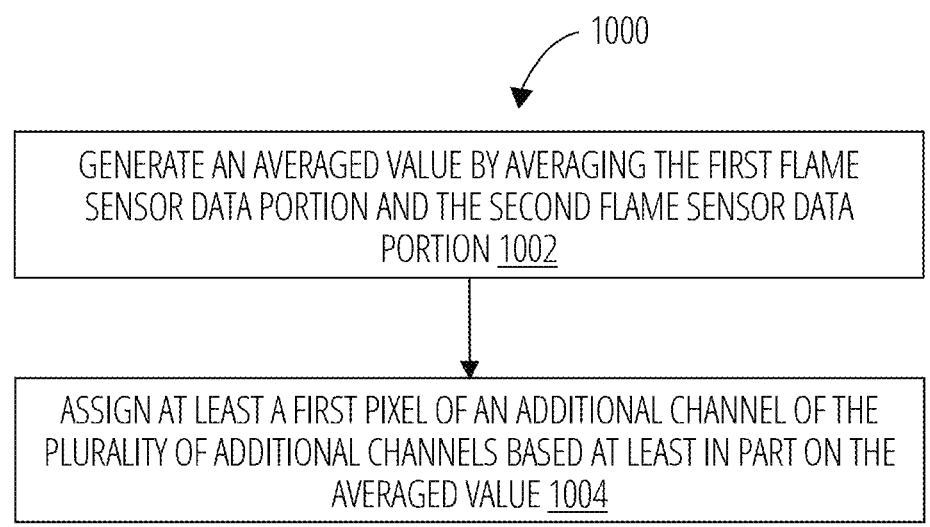
FIG. 10 illustrates a process 1000 for assigning a pixel value based on an averaged value of flame sensor data in accordance with at least some example embodiments of the present disclosure.

FIG. 10 illustrates a process 1000 for assigning a pixel value based on an averaged value of flame sensor data in accordance with at least some example embodiments of the present disclosure. In some embodiments, the process 1000 is embodied by computer program code stored on a non-transitory computer-readable storage medium of a computer program product configured for execution to perform the process as depicted and described. Alternatively or additionally, in some embodiments, the process 1000 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with an end-user computing device, sensor(s), alert system(s), and/or the like. For purposes of simplifying the description, the process 1000 is described as performed by and from the perspective of the apparatus 200.

The process 1000 begins at operation 1002. In some embodiments, the process 1000 begins after one or more operations depicted and/or described with respect to any one of the other processes described herein. For example, in some embodiments as depicted, the process 1000 begins after execution of operation 702. In this regard, some or all of the process 900 may replace or supplement one or more blocks depicted and/or described with respect to any of the processes described herein. Upon completion of the process 900, the flow of operations may terminate. Additionally or alternatively, as depicted, upon completion of the process 900 in some embodiments, flow may return to one or more operation(s) of another process, such as the operation 704. It will be appreciated that, in some embodiments, the process 900 embodies a sub-process of one or more other process(es) depicted and/or described herein, for example the process 700.

In operation 1002, generate an averaged value by averaging the first flame sensor data portion and the second flame sensor data portion. In some embodiments, the apparatus 200 generates the averaged value by averaging the first flame sensor data portion and the second flame sensor data portion. In some embodiments, the averaged value comprises a simple average of a plurality of flame sensor data portions, including at least the first flame sensor data portion and the second flame sensor data portion. Alternatively or additionally, in some embodiments, the averaged value comprises a weighted average of a plurality of flame sensor data portions, including at least the first flame sensor data portion and the second flame sensor data portion.

In some embodiments, the first flame sensor data portion and the second flame sensor data portion correspond to sequentially captured samples. For example, the second flame sensor data portion may be captured after the first flame sensor data portion by a particular flame sensor. In some such contexts, the averaged value may be generated corresponding to a different sampling rate than the sampling rates corresponding to individual first and second flame sensor data portions. Alternatively or additionally, in some embodiments, the first flame sensor data portion and the second flame sensor data portion are captured by different flame sensors associated with the same environment or sub-region of the environment. In some such embodiments, all flame sensor data portions from flame sensors corresponding to the sub-region may be averaged to determine a value for the sub-region associated with a particular sampling time (e.g., corresponding to samples captured at the same timestamp or within a particular interval from one another).

In operation 1004, assign at least a first pixel of an additional channel of the plurality of additional channels based at least in part on the averaged value. In some embodiments, the flame sensor data is utilized to assign a pixel value for each of a plurality of additional channels. For example, different data values of a portion of flame sensor data (e.g., associated with different frequency bands in the context of IR flame sensor data for example) may be utilized to assign pixel values to a different channel for each different data value. In some embodiments, the additional channel to be set by the data values for the particular flame sensor data portion is predetermined.

In some embodiments, for example, the pixel is assigned to the averaged value in a particular channel. In some embodiments, the apparatus 200 continues to assign pixel values until all pixels for all channels in a particular data-constructed image have been assigned. The data-constructed image is then stored and/or outputted for further processing, as described herein.

In some embodiments, pixel values for each channel of a plurality of channels are assigned in parallel. For example, a first channel associated with pixel values assigned based at least in part on gas sensor data may be assigned in parallel with one or more additional channels assigned based at least in part on flame sensor data. In this regard, the data-constructed image may be formed with improved efficiency. In other embodiments, pixel values for channels are assigned serially, such that one channel is processed at a time.

Figure 11:
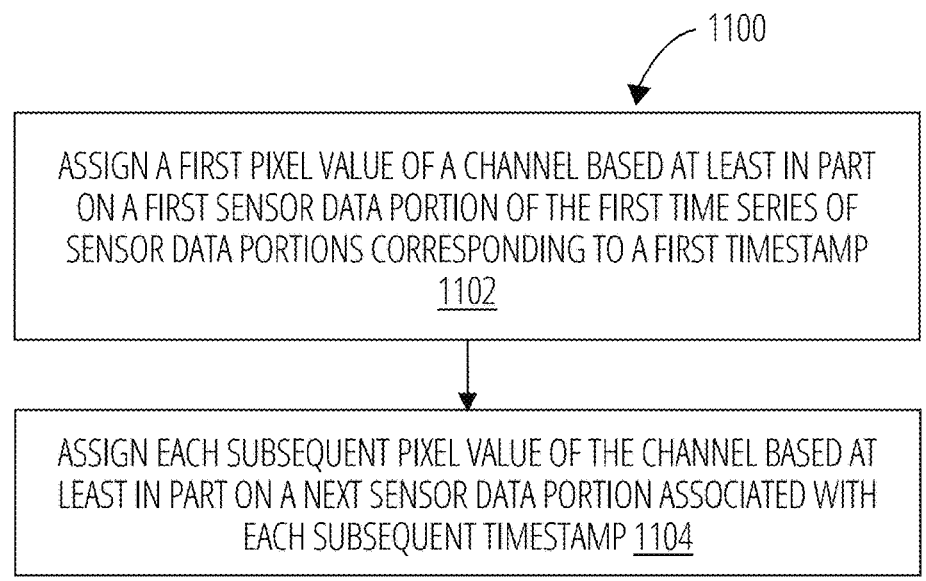
FIG. 11 illustrates a process 1100 for assigning pixel values in a sequence over a timestamp interval in accordance with at least some example embodiments of the present disclosure.

FIG. 11 illustrates a process 1100 for assigning pixel values in a sequence over a timestamp interval in accordance with at least some example embodiments of the present disclosure. In some embodiments, the process 1100 is embodied by computer program code stored on a non-transitory computer-readable storage medium of a computer program product configured for execution to perform the process as depicted and described. Alternatively or additionally, in some embodiments, the process 1100 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with an end-user computing device, sensor(s), alert system(s), and/or the like. For purposes of simplifying the description, the process 1100 is described as performed by and from the perspective of the apparatus 200.

The process 1100 begins at operation 1102. In some embodiments, the process 1100 begins after one or more operations depicted and/or described with respect to any one of the other processes described herein. For example, in some embodiments as depicted, the process 1100 begins after execution of operation 702. In this regard, some or all of the process 1100 may replace or supplement one or more blocks depicted and/or described with respect to any of the processes described herein. Upon completion of the process 1100, the flow of operations may terminate. Additionally or alternatively, as depicted, upon completion of the process 1100 in some embodiments, flow may return to one or more operation(s) of another process, such as the operation 704. It will be appreciated that, in some embodiments, the process 1100 embodies a sub-process of one or more other process(es) depicted and/or described herein, for example the process 700.

In operation 1102, the process 1100 assigns a first pixel value of a channel based at least in part on a first sensor data portion of the first time series of sensor data portions, the first sensor data portion corresponding to a first timestamp. In this regard, the first sensor data may be captured associated with a particular sample interval, for example determined based at least in part on a sampling rate for the sensor that captured the particular first sensor data portion. The particular sensor(s) that captured the first sensor data portion may continue to capture subsequent sensor data portions, each associated with a subsequent timestamp. In this regard, the apparatus 200 may receive any number of sensor data portions from a particular sensor, each associated with a particular timestamp or timestamp interval.

In operation 1104, the process 1100 assigns each subsequent pixel value of the first channel based at least in part on a next gas sensor data portion associated with each subsequent timestamp. In some embodiments, the apparatus 200 assigns pixel values to pixels sequentially, for example starting from a determinable starting pixel and progressing linearly in a particular direction (e.g., along an x-axis or a y-axis of the pixels). Alternatively or additionally, in some embodiments the apparatus 200 determines a subsequent pixel to be assigned based on another determinable pattern, pixel selection algorithm, and/or the like. For example, in some embodiments, the apparatus 200 assigns pixels radially beginning from a determinable starting pixel. The pixels values may be assigned based at least in part on the sensor data portions received in chronological order, based at least in part on the timestamp and/or timestamp intervals associated with such sensor data portion(s).

Figure 12:
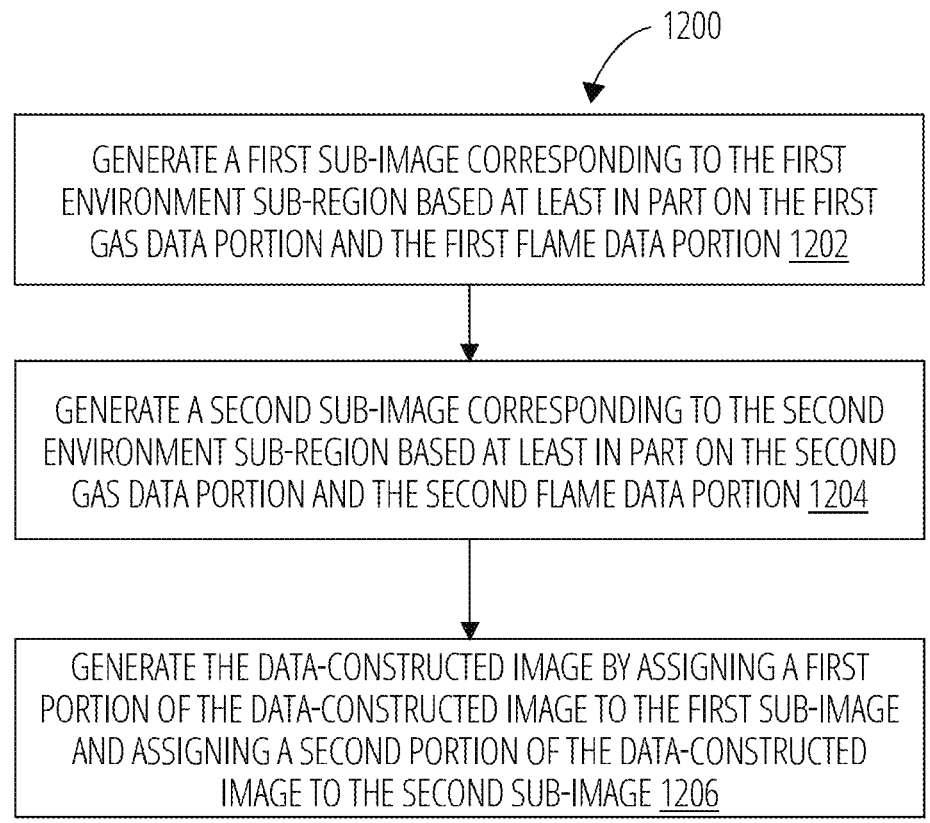
FIG. 12 illustrates a process 1200 for generating a data-constructed image based at least in part on a plurality of sub-images in accordance with at least some example embodiments of the present disclosure.

FIG. 12 illustrates a process 1200 for generating a data-constructed image based at least in part on a plurality of sub-images in accordance with at least some example embodiments of the present disclosure. In some embodiments, the process 1200 is embodied by computer program code stored on a non-transitory computer-readable storage medium of a computer program product configured for execution to perform the process as depicted and described. Alternatively or additionally, in some embodiments, the process 1200 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with an end-user computing device, sensor(s), alert system(s), and/or the like. For purposes of simplifying the description, the process 1200 is described as performed by and from the perspective of the apparatus 200.

The process 1200 begins at operation 1202. In some embodiments, the process 1200 begins after one or more operations depicted and/or described with respect to any one of the other processes described herein. For example, in some embodiments as depicted, the process 1200 begins after execution of operation 702. In this regard, some or all of the process 1200 may replace or supplement one or more blocks depicted and/or described with respect to any of the processes described herein. Upon completion of the process 1200, the flow of operations may terminate. Additionally or alternatively, as depicted, upon completion of the process 1200 in some embodiments, flow may return to one or more operation(s) of another process, such as the operation 704. It will be appreciated that, in some embodiments, the process 1200 embodies a sub-process of one or more other process(es) depicted and/or described herein, for example the process 700.

In operation 1202, the process 1200 generates a first sub-image corresponding to the first environment sub-region based at least in part on the first gas sensor data portion and the first flame sensor data portion. In some embodiments, for example, the apparatus 200 generates a first sub-image by generating a plurality of channels based at least in part on the first gas data portion and the first flame sensor data portion. In this regard, the first gas sensor data portion may be utilized to assign a pixel value for a first channel of the sub-image, and the first flame sensor data portion may be utilized to assign a pixel value for a plurality of additional channels of the sub-image (e.g., based at least in part on different data values for the first portion of flame sensor data). It will be appreciated that each channel of the sub-image may in and of itself embody a secondary sub-image (e.g., the secondary sub-image comprising a single channel).

In operation 1204, the process 1200 generates a second sub-image corresponding to the second environment region based at least in part on the second gas data portion and the second flame data portion. It will be appreciated that the second sub-image may be similarly assigned to a new image (e.g., the second sub-image) in the same manner as described with respect to operation 1202. For example, in some embodiments the apparatus 200 generates the second sub-image by generating a plurality of channel based at least in part on the second gas data portion and the second flame sensor data portion, such as by assigning pixel values to channels of the second sub-image.

In operation 1206, the process 1200 generates the data-constructed image by assigning a first portion of the data-constructed image to the first sub-image and assigning a second portion of the data-constructed image to the second sub-image. In some embodiments, the first portion of the data-constructed image corresponds to a first determinable pixel sub-region. Additionally or alternatively, in some embodiments the second portion of the data-constructed image corresponds to a second determinable pixel sub-region. In some embodiments the apparatus 200 maintains a predefined schema of pixel sub-regions associated with particular sub-regions of an environment, for example the first environment sub-region and the second environment sub-region. In this regard, the apparatus 200 may utilize the sub-image generated utilizing sensor data captured from the particular sub-region to assign the generated sub-image to the predefined pixel sub-region corresponding to the environment sub-region. In this regard, it will be appreciated that the first sub-image and the second sub-image may be associated with different pixel sub-regions and thus utilized to assign different pixels of the entire data-constructed image. Additionally or alternatively, in some embodiments the apparatus 200 appends the first sub-image with the second sub-image, stitches the first sub-image with the second sub-image, or otherwise combines the first sub-image with the second sub-image to generate the data-constructed image including the pixel values of both sub-images.

Figure 13:
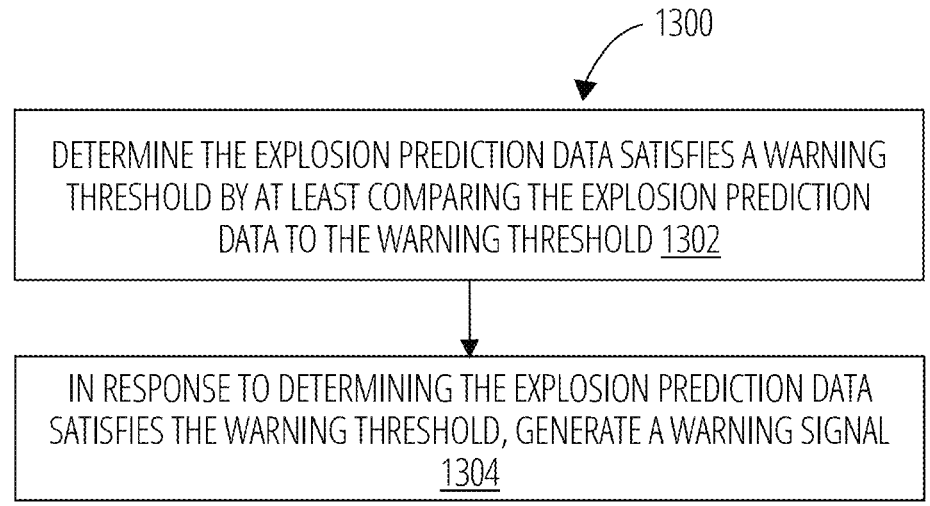
FIG. 13 illustrates a process 1300 for generating a warning signal in accordance with at least some example embodiments of the present disclosure.

FIG. 13 illustrates a process 1300 for generating a warning signal in accordance with at least some example embodiments of the present disclosure. In some embodiments, the process 1300 is embodied by computer program code stored on a non-transitory computer-readable storage medium of a computer program product configured for execution to perform the process as depicted and described. Alternatively or additionally, in some embodiments, the process 1300 is performed by one or more specially configured computing devices, such as the apparatus 200 alone or in communication with one or more other component(s), device(s), system(s), and/or the like. In this regard, in some such embodiments, the apparatus 200 is specially configured by computer-coded instructions (e.g., computer program instructions) stored thereon, for example in the memory 204 and/or another component depicted and/or described herein and/or otherwise accessible to the apparatus 200, for performing the operations as depicted and described. In some embodiments, the apparatus 200 is in communication with one or more external apparatus(es), system(s), device(s), and/or the like, to perform one or more of the operations as depicted and described. For example, the apparatus 200 in some embodiments is in communication with an end-user computing device, sensor(s), alert system(s), and/or the like. For purposes of simplifying the description, the process 1300 is described as performed by and from the perspective of the apparatus 200.

The process 1300 begins at operation 1302. In some embodiments, the process 1300 begins after one or more operations depicted and/or described with respect to any one of the other processes described herein. For example, in some embodiments as depicted, the process 1300 begins after execution of operation 710. In this regard, some or all of the process 1300 may replace or supplement one or more blocks depicted and/or described with respect to any of the processes described herein. Upon completion of the process 1300, the flow of operations may terminate. Additionally or alternatively, as depicted, upon completion of the process 1300 in some embodiments, flow may return to one or more operation(s) of another process, such as the operation 702. It will be appreciated that, in some embodiments, the process 1300 embodies a sub-process of one or more other process(es) depicted and/or described herein, for example the process 700.

In operation 1302, the process 1300 determines the explosion prediction data satisfies a warning threshold. In some embodiments, the warning threshold indicates a cutoff that, if satisfies, indicates a warning regarding a likelihood of explosion in at least a sub-region of an environment is necessary. In some embodiments, the apparatus 200 determines the explosion prediction data satisfies the warning threshold by at least comparing the explosion prediction data to the threshold. In some embodiments, the warning threshold embodies a maximum probability that, if exceeded or otherwise satisfied, indicates a warning should be outputted. In some embodiments, the warning threshold embodies one or more discrete data values, for example that indicate a dangerous environment. It will be appreciated that in some embodiments, the comparison may be performed in any manner that determines whether the explosion prediction data indicates one or more region(s) of the environment are dangerous due to an unacceptable risk of explosion within said region(s).

In operation 1304, the process 1300 in response to determining the explosion prediction data satisfies the threshold, generates a warning signal. In some embodiments, the warning signal embodies data that facilitates output of at least one alert. The warning signal may trigger generation, transmission, and/or output of an audio alert, visual alert, user interface alert, pop-up, siren, user device notification, email, and/or the like. In some embodiments, a plurality of warning signals are generated that cause output of a plurality of alerts. For example, in one example context, one or more warning signal(s) is/are generated that facilitate transmission of an alert to a user device associated with an emergency response and/or repair team associated with a particular environment or sub-region thereof, and/or that activates an alert system in the environment and/or sub-region thereof that is determined at risk of explosion based at least in part on the explosion prediction data.

CONCLUSION

Although an example processing system has been described above, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a repository management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any disclosures or of what may be claimed, but rather as descriptions of features specific to particular embodiments of particular disclosures. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A computer-implemented method comprising:

receiving a plurality of gas sensor data and a plurality of flame sensor data;

generating a data-constructed image comprising a plurality of channels, the plurality of channels comprising at least a first channel assigned based at least in part on the plurality of gas sensor data and at least one additional channel assigned based at least in part on the plurality of flame sensor data; and generating explosion prediction data by applying at least a portion of the data-constructed image to a prediction model, wherein the prediction model generates the explosion prediction data based at least in part on explosion feature data determined from at least the plurality of channels corresponding to at least the portion of the data-constructed image, wherein the plurality of gas sensor data comprises at least a first gas sensor data portion and a second gas sensor data portion captured via a first gas sensor, wherein the first gas sensor data portion is associated with a first sampling rate, wherein the plurality of flame sensor data comprises at least a first flame sensor data portion captured via a first flame sensor associated with a second sampling rate, wherein the first sampling rate is faster than the second sampling rate, wherein generating the data-constructed image comprises:

generating an averaged value by averaging the first gas sensor data portion and the second gas sensor data portion; and assigning at least a first pixel of the first channel based at least in part on the averaged value.

2. The computer-implemented method of claim 1, the computer-implemented method further comprising:

applying the data-constructed image to a computer vision model that identifies at least the portion of the data-constructed image determined associated with at least one explosion contribution level indicating presence of at least one explosion contributing factor in an environment; and extracting the portion of the data-constructed image from the data-constructed image, wherein the prediction model only processes the extracted portion of the data-constructed image.

3. The computer-implemented method of claim 1, wherein the plurality of flame sensor data comprises at least the first flame sensor data portion and a second flame sensor data portion captured via the first flame sensor associated with the second sampling rate, wherein generating the data-constructed image comprises:

generating an additional averaged value by averaging the first flame sensor data portion and the second flame sensor data portion; and assigning at least an additional first pixel of an additional channel of a plurality of additional channels based at least in part on the additional averaged value.

4. The computer-implemented method of claim 1, wherein the plurality of gas sensor data comprises a first time series of gas sensor data portions captured via at least one gas sensor, and wherein generating the data-constructed image comprises:

assigning a first pixel value of the first channel based at least in part on the first gas sensor data portion of the first time series of gas sensor data portions corresponding to a first timestamp; and assigning each subsequent pixel value of the first channel based at least in part on a next gas sensor data portion associated with each subsequent timestamp.

5. The computer-implemented method of claim 1, wherein the plurality of flame sensor data comprises at least first band range data, second band range data, and third band range data, wherein the at least one additional channel comprises a second channel, a third channel, and a fourth channel, and wherein generating the data-constructed image comprises:

assigning the second channel based at least in part on the first band range data;

assigning the third channel based at least in part on the second band range data; and assigning the fourth channel based at least in part on the third band range data.

6. The computer-implemented method of claim 1, the computer-implemented method further comprising:

applying the data-constructed image to a computer vision model that at least determines an explosion contribution level; and determining the explosion contribution level satisfies a threshold, wherein the generating the explosion prediction data is initiated in response to determining that the explosion contribution level satisfies the threshold.

7. The computer-implemented method of claim 1, wherein the plurality of gas sensor data is collected via a plurality of gas sensors.

8. The computer-implemented method of claim 1, wherein the plurality of flame sensor data is collected via a plurality of flame sensors.

9. The computer-implemented method of claim 1, wherein the first gas sensor data portion corresponds to a first environment region and the second gas sensor data portion is associated with a second gas sensor and corresponds to a second environment region, and wherein the plurality of flame sensor data comprises the first flame sensor data portion associated with the first flame sensor corresponding to the first environment region and a second flame sensor data portion associated with a second flame sensor corresponding to the second environment region, wherein generating the data-constructed image comprises:

generating a first sub-image corresponding to the first environment region based at least in part on the first gas sensor data portion and the first flame sensor data portion;

generating a second sub-image corresponding to the second environment region based at least in part on the second gas sensor data portion and the second flame sensor data portion; and generating the data-constructed image by assigning a first portion of the data-constructed image to the first sub-image and assigning a second portion of the data-constructed image to the second sub-image.

10. The computer-implemented method of claim 1, wherein the data-constructed image comprises a plurality of sub-image, each sub-image corresponding to an assigned pixel sub-region of the data-constructed image.

11. The computer-implemented method of claim 1, wherein the explosion prediction data comprises a data value indicating a probability of an explosion.

12. The computer-implemented method of claim 1, the computer-implemented method further comprising:

determining the explosion prediction data satisfies a threshold by at least comparing the explosion prediction data to the threshold; and in response to determining the explosion prediction data satisfies the threshold, generating a warning signal.

13. The computer-implemented method of claim 1, wherein the prediction model comprises a specially trained machine learning model.

14. A computing apparatus comprising:

at least one processor; and at least one memory storing instructions that, when executed by the at least one processor, configure the computing apparatus to:

receive a plurality of gas sensor data and a plurality of flame sensor data;

generate a data-constructed image comprising a plurality of channels, the plurality of channels comprising at least a first channel assigned based at least in part on the plurality of gas sensor data and at least one additional channel assigned based at least in part on the plurality of flame sensor data; and generate explosion prediction data by applying at least a portion of the data-constructed image to a prediction model, wherein the prediction model generates the explosion prediction data based at least in part on explosion feature data determined from at least the plurality of channels corresponding to at least the portion of the data-constructed image, wherein the plurality of gas sensor data comprises at least a first gas sensor data portion and a second gas sensor data portion captured via a first gas sensor, wherein the first gas sensor data portion is associated with a first sampling rate, wherein the plurality of flame sensor data comprises at least a first flame sensor data portion captured via a first flame sensor associated with a second sampling rate, wherein the first sampling rate is faster than the second sampling rate, wherein generating the data-constructed image comprises:

generating an averaged value by averaging the first gas sensor data portion and the second gas sensor data portion; and assigning at least a first pixel of the first channel based at least in part on the averaged value.

15. The computing apparatus of claim 14, wherein the plurality of flame sensor data comprises at least first band range data, second band range data, and third band range data, wherein the at least one additional channel comprises a second channel, a third channel, and a fourth channel, and wherein to generate the data-constructed image the computing apparatus is configured to:
assign the second channel based at least in part on the first band range data;
assign the third channel based at least in part on the second band range data; and
assign the fourth channel based at least in part on the third band range data.

16. The computing apparatus of claim 14, wherein the instructions further configure the computing apparatus to:
apply the data-constructed image to a computer vision model that at least determines an explosion contribution level; and
determine the explosion contribution level satisfies a threshold,
wherein the generating the explosion prediction data is initiated in response to determining that the explosion contribution level satisfies the threshold.

17. The computing apparatus of claim 14, wherein the first gas sensor data portion corresponds to a first environment region and the second gas sensor data portion is associated with a second gas sensor and corresponds to a second environment region, and wherein the plurality of flame sensor data comprises the first flame sensor data portion associated with the first flame sensor corresponding to the first environment region and a second flame sensor data portion associated with a second flame sensor corresponding to the second environment region, wherein generating the data-constructed image comprises:
generate a first sub-image corresponding to the first environment region based at least in part on the first gas sensor data portion and the first flame sensor data portion;
generate a second sub-image corresponding to the second environment region based at least in part on the second gas sensor data portion and the second flame sensor data portion; and
generate the data-constructed image by assigning a first portion of the data-constructed image to the first sub-image and assigning a second portion of the data-constructed image to the second sub-image.

18. A non-transitory computer-readable storage medium, the non-transitory computer-readable storage medium comprising one or more instructions that when executed by at least one processor, cause the at least one processor to:
receive a plurality of gas sensor data and a plurality of flame sensor data;
generate a data-constructed image comprising a plurality of channels, the plurality of channels comprising at least a first channel assigned based at least in part on the plurality of gas sensor data and at least one additional channel assigned based at least in part on the plurality of flame sensor data; and
generate explosion prediction data by applying at least a portion of the data-constructed image to a prediction model,
wherein the prediction model generates the explosion prediction data based at least in part on explosion feature data determined from at least the plurality of channels corresponding to at least the portion of the data-constructed image,
wherein the plurality of gas sensor data comprises at least a first gas sensor data portion and a second gas sensor data portion captured via a first gas sensor, wherein the first gas sensor data portion is associated with a first sampling rate,
wherein the plurality of flame sensor data comprises at least a first flame sensor data portion captured via a first flame sensor associated with a second sampling rate, wherein the first sampling rate is faster than the second sampling rate,
wherein generating the data-constructed image comprises:
generating an averaged value by averaging the first gas sensor data portion and the second gas sensor data portion; and
assigning at least a first pixel of the first channel based at least in part on the averaged value.

19. The non-transitory computer-readable storage medium of claim 18, wherein the first gas sensor data portion corresponds to a first environment region and the second gas sensor data portion is associated with a second gas sensor and corresponds to a second environment region, and wherein the plurality of flame sensor data comprises the first flame sensor data portion associated with the first flame sensor corresponding to the first environment region and a second flame sensor data portion associated with a second flame sensor corresponding to the second environment region, wherein generating the data-constructed image comprises:
generate a first sub-image corresponding to the first environment region based at least in part on the first gas sensor data portion and the first flame sensor data portion;
generate a second sub-image corresponding to the second environment region based at least in part on the second gas sensor data portion and the second flame sensor data portion; and
generate the data-constructed image by assigning a first portion of the data-constructed image to the first sub-image and assigning a second portion of the data-constructed image to the second sub-image.

* * * * *